(12) United States Patent
Ueno

(10) Patent No.: US 12,398,170 B2
(45) Date of Patent: Aug. 26, 2025

(54) NUCLEOSIDE DERIVATIVE AND USE THEREOF

(71) Applicants: National University Corporation Tokai National Higher Education and Research System, Nagoya (JP); Yamasa Corporation, Choshi (JP)

(72) Inventor: Yoshihito Ueno, Gifu (JP)

(73) Assignees: National University Corporation Tokai National Higher Education and Research System, Nagoya (JP); Yamasa Corporation, Choshi (JP)

( * ) Notice: Subject to any disclaimer, the term of this patent is extended or adjusted under 35 U.S.C. 154(b) by 797 days.

(21) Appl. No.: 17/771,089

(22) PCT Filed: Oct. 28, 2020

(86) PCT No.: PCT/JP2020/040526
§ 371 (c)(1),
(2) Date: Apr. 22, 2022

(87) PCT Pub. No.: WO2021/085509
PCT Pub. Date: May 6, 2021

(65) Prior Publication Data
US 2023/0011179 A1    Jan. 12, 2023

(30) Foreign Application Priority Data
Oct. 28, 2019   (JP) ................. 2019-195664

(51) Int. Cl.
*C07H 19/06*    (2006.01)
*C07H 21/02*    (2006.01)
*C12N 15/113*   (2010.01)

(52) U.S. Cl.
CPC ............ *C07H 19/06* (2013.01); *C07H 21/02* (2013.01); *C12N 15/113* (2013.01); *C12N 2310/14* (2013.01)

(58) Field of Classification Search
None
See application file for complete search history.

(56) References Cited

U.S. PATENT DOCUMENTS 5,446,137 A      8/1995  Maag et al.
2021/0371447 A1  12/2021 Ueno

FOREIGN PATENT DOCUMENTS

| CN | 110204583 A | 9/2019 | | |
|---|---|---|---|---|
| JP | 2002-521310 A | 7/2002 | | |
| WO | WO-2018110678 A1 | * | 6/2018 | ............. A61K 47/26 |
| WO | WO-2021000380 A1 | * | 1/2021 | ............... C07H 1/00 |

OTHER PUBLICATIONS

Gore et al., Synthesis, gene silencing, and molecular modeling studies of 4'-C-aminomethyl-2'-O-methyl modified small interfering RNAs. J Org Chem. Apr. 6, 2012;77(7):3233-45.
Gore et al., Influence of 2'-fluoro versus 2'-O-methyl substituent on the sugar puckering of 4'-C-aminomethyluridine. J Org Chem. Oct. 4, 2013;78(19):9956-62.
Pfundheller et al., Oligonucleotides containing 4'-C-aminomethyl-2'-modified thymidines show increased binding affinity towards DNA and RNA. Bioorg Med Chem Lett. Sep. 20, 1999;9(18):2667-72.
Pfundheller et al., Oligonucleotides Containing Novel 4'-C- or 3'-C-(Aminoalkyl)-Branched Thymidines1. Helvetica Chimica Acta. Jan. 19, 2000;83(1):128-51.
International Search Report and Written Opinion mailed Dec. 8, 2020 in corresponding PCT application No. PCT/JP2020/040526.
International Preliminary Report on Patentability issued May 12, 2022 in corresponding PCT application No. PCT/JP2020/040526.
Kano et al., Synthesis and properties of 4'-C-aminoalkyl-2'-fluoro-modified RNA oligomers. Bioorg Med Chem. Aug. 15, 2018;26(15):4574-4582.
Koizumi et al., Synthesis of 4'-C-aminoalkyl-2'-O-methyl modified RNA and their biological properties. Bioorg Med Chem. Jul. 23, 2018;26(12):3521-3534.

* cited by examiner

*Primary Examiner* — Traviss C McIntosh, III
(74) *Attorney, Agent, or Firm* — Nields, Lemack & Frame, LLC

(57) ABSTRACT

Provided is a nucleoside derivative represented by the following formula (1):

or a salt thereof, wherein $R^1$ represents an alkoxy group, a hydrogen atom or a halogen atom; $R^2$ and $R^4$, which may be the same as or different from each other, each represents a hydrogen atom, a protective group for a hydroxyl group, a phosphate group, a protected phosphate group, or $-P(=O)_nR^5R^6$ in which n represents 0 or 1, $R^5$ and $R^6$, which may be the same as or different from each other, each represents a hydrogen atom, a hydroxyl group, a protected hydroxyl group, a mercapto group, a protected mercapto group, an alkoxy group, a cyanoalkoxy group, an amino group, or a substituted amino group, provided that when n is 1, both $R^5$ and $R^6$ cannot be the hydrogen atom at the same time; $R^3$ represents $-(CH_2)_mNHR^7$ in which m represents an integer of 1 to 6, $R^7$ represents a hydrogen atom, an alkyl group, an alkenyl group or a protective group for an amino group; and B represents a purin-9-yl group, a 2-oxo-pyrimidin-1-yl group, a substituted purin-9-yl group, or a substituted 2-oxo-pyrimidin-1-yl group.

5 Claims, 3 Drawing Sheets
Specification includes a Sequence Listing.

```
                        SEQUENCE LISTING

<160> NUMBER OF SEQ ID NOS: 4

<210> SEQ ID NO 1
<211> LENGTH: 11
<212> TYPE: RNA
<213> ORGANISM: Artificial Sequence
<220> FEATURE:
<223> OTHER INFORMATION: sense chain in Duplexes 1-3

<400> SEQUENCE: 1
uucuucuucu u                                                              11

<210> SEQ ID NO 2
<211> LENGTH: 11
<212> TYPE: RNA
<213> ORGANISM: Artificial Sequence
<220> FEATURE:
<223> OTHER INFORMATION: antisense chain in Duplexes 1-3

<400> SEQUENCE: 2
aagaagaaga a                                                              11

<210> SEQ ID NO 3
<211> LENGTH: 21
<212> TYPE: RNA
<213> ORGANISM: Artificial Sequence
<220> FEATURE:
<223> OTHER INFORMATION: sense chain in siRNA 1-7

<400> SEQUENCE: 3
ggccuuucac uacuaauacu u                                                   21

<210> SEQ ID NO 4
<211> LENGTH: 21
<212> TYPE: DNA
<213> ORGANISM: Artificial Sequence
<220> FEATURE:
<223> OTHER INFORMATION: antisense chain in siRNA 1-7

<400> SEQUENCE: 4
ttccggaaag ugaugaggau g                                                   21
```

NUCLEOSIDE DERIVATIVE AND USE THEREOF

FIELD OF THE INVENTION

The present disclosure relates to a nucleoside derivative and use thereof.

BACKGROUND OF THE INVENTION

There are many known diseases such as cancers that would be in relation to gene mutations or abnormal gene expressions. Nucleic acid drugs such as siRNAs and antisense nucleic acids, which suppress gene expressions, are useful for such diseases and can have higher pharmaceutical potentials. For example, siRNA is a double-stranded RNA, and when introduced into cytoplasm, the siRNA interacts with proteins such as Argonaute 2 (Ago 2) to form a complex called RISC (RNA-induced silencing complex). One strand of the double strand of siRNA is then cleaved to form a single strand in the RISC, so that mature RISC is formed. In this case, the strand that is cleaved and removed from the RISC is referred to as a passenger strand, and the strand that remains in the mature RISC is referred to as a guide strand. The guide strand of the mature RISC recognizes nRNA with a complementary sequence, which is cleaved and degraded by an endonuclease activity of Ago 2, thereby suppressing an expression of a target gene.

On the other hand, siRNA has problems of difficulty in penetrating cell membranes and being easily degraded by nucleases. Further, although siRNA has higher target selectivity, it has a problem that it is difficult to be selectively transported to a target tissue. To address these problems, delivery carriers such as lipid nanoparticles (LNPs) are being studied. Furthermore, attempts have been proposed to modify the delivery carriers, such as by introducing aminomethyl groups into sugar moieties (ribose) of nucleoside derivatives or their salts, which are elements of RNAs (Non-Patent Literatures 1 to 4).

However, the attempts of the prior arts could not result in satisfactory delivery carriers, and could not satisfy sufficient cell membrane permeability, ribonuclease resistance, and target tissue deliverability even by the modification of the sugar moieties (ribose) of the nucleoside derivatives.

Therefore, a technique has been proposed to improve properties such as ribonuclease resistance and cell membrane permeability by introducing a basic substituent(s) such as an amino group into a sugar moiety (ribose or deoxyribose) of a nucleoside derivative or a salt thereof (which may hereinafter be abbreviated as a "nucleoside derivative") at the 4' position or by substituting a hydroxyl group at the 2' position with a halogen atom (Patent Literature 1).

CITATION LIST

Patent Literature

[Patent Literature 1] WO 2018/110678 A1

Non-Patent Literatures

[Non-Patent Literature 1] HELVATICA CHIMICA ACTA Vol. 83, (2000), 128-151
[Non-Patent Literature 2] The Journal of Organic Chemistry 2012, 77, 3233-3245
[Non-Patent Literature 3] Bioorganic & Chemistry letters (1999), 2667-2672
[Non-Patent Literature 4] The Journal of Organic Chemistry 2013, 78, 9956-9962

SUMMARY OF THE INVENTION

Problem to be Solved by the Invention

In siRNA, the puckering of the sugar moiety (ribose or deoxyribose) of the nucleoside derivative, which is a component of double-stranded RNA, affects the formation of the double strand. In general, the puckering of the sugar moiety is of N-type (C3'-endo) and S-type (C2'-endo); the N-type sugar moiety has a higher affinity for single-stranded RNA, while the S-type sugar moiety has a higher affinity for single-stranded DNA. Therefore, thermal stability of double-stranded RNA can be improved by increasing a ratio of the N-type sugar moiety present.

However, when the basic substituent such as an amino group is introduced into the sugar moiety (ribose or deoxyribose) at the 4' position, the substituent interacts with the group at the 2' position, and the sugar moiety tends to be biased from the N-type to the S-type, which may reduce the thermal stability of the double-stranded RNA.

The present invention has been made in order to solve the above problems. An object of the present invention is to provide a nucleoside derivative or a salt thereof, which can provide an oligonucleotide derivative or a salt thereof with higher thermal stability when used as a component of a double-stranded nucleic acid such as double-stranded RNA.

Also, an object of the present invention is to provide an oligonucleotide derivative or a salt thereof, which has higher thermal stability when it forms a double-stranded nucleic acid such as double-stranded RNA, and which can have a sufficient ability to suppress gene expression as a nucleic acid medicine such as siRNA.

Methods for Solving the Problem

The present inventors have focused on the structure of the sugar moiety (ribose or deoxyribose) of the nucleoside derivative to solve the above problems. As a result of their intensive studies, they have found that the ratio of the N-type sugar moiety present could be increased by introducing a basic substituent such as an aminoalkyl group via an oxygen atom into the sugar moiety at the 4' position, and they have completed the present invention.

Thus, the present invention relates to a nucleoside derivative represented by the following formula (1), or a salt thereof:

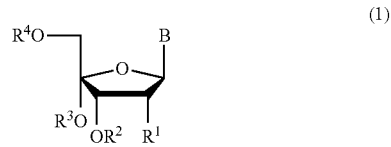

(1)

In the formula, $R^1$ represents an alkoxy group, a hydrogen atom or a halogen atom; $R^2$ and $R^4$, which may be the same as or different from each other, each represents a hydrogen atom, a protective group for a hydroxyl group, a phosphate group, a protected phosphate group, or $-P(=O)_nR^5R^6$ in which n represents 0 or 1, $R^5$ and $R^6$, which may be the same as or different from each other, each represents a hydrogen atom, a hydroxyl group, a protected hydroxyl group, a mercapto group, a protected mercapto group, an alkoxy group, a cyanoalkoxy group, an amino group, or a substituted amino group, provided that when n is 1, both $R^5$ and $R^6$ cannot be the hydrogen atom at the same time; $R^3$ represents —$(CH_2)_m NHR^7$ in which m represents an integer of 1 to 6, $R^7$ represents a hydrogen atom, an alkyl group, an alkenyl group or a protective group for an amino group; and B represents a purin-9-yl group, a 2-oxo-pyrimidin-1-yl group, a substituted purin-9-yl group, or a substituted 2-oxo-pyrimidin-1-yl group.

The present invention also relates to an oligonucleotide derivative comprising at least one partial structure represented by the following formula (2), or a salt thereof:

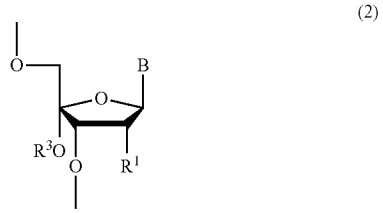
(2)

In the formula, $R^1$ represents an alkoxy group, a hydrogen atom, or a halogen atom; $R^3$ represents —$(CH_2)_m NHR^7$ in which m represents an integer of 1 to 6, and $R^7$ represents a hydrogen atom, an alkyl group, an alkenyl group, or a protective group for an amino group; and B represents a purin-9-yl group, a 2-oxo-pyrimiclin-1-yl group, a substituted purin-9-yl group, or a substituted 2-oxo-pyrimidin-1-yl group.

Further, the present invention relates to an siRNA comprising the above oligonucleotide derivative or salt thereof as an active ingredient.

Effects of Invention

According to the nucleoside derivative or salt thereof according to the present invention, it is possible to obtain an oligonucleotide derivative or a salt thereof with higher thermal stability when used as a component of a double-stranded nucleic acid such as double-stranded RNA.

Also, according to the oligonucleotide derivative or salt thereof according to the present invention, it is possible to have higher thermal stability when it forms a double-stranded nucleic acid such as double-stranded RNA, and to have a sufficient ability to suppress gene expression as a nucleic acid medicine such as siRNA.

DETAILED DESCRIPTION OF THE INVENTION

Figure 1:
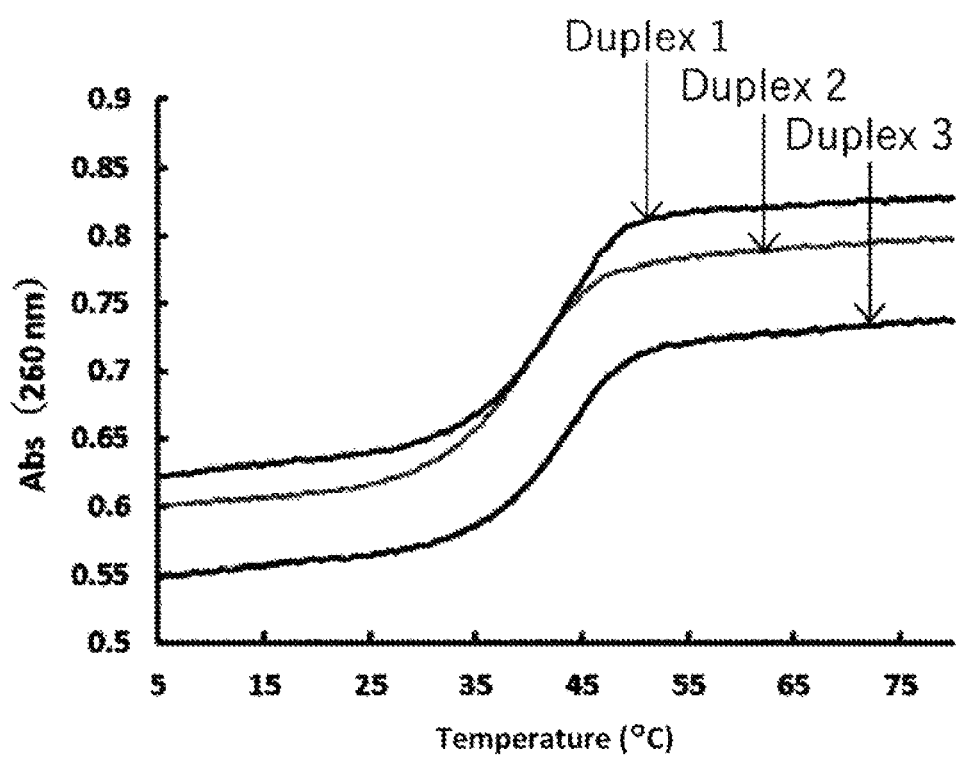
FIG. 1 is melting curves showing evaluation results of thermal stability for Duplexes 1 to 3 synthesized in Examples.
Figure 2:
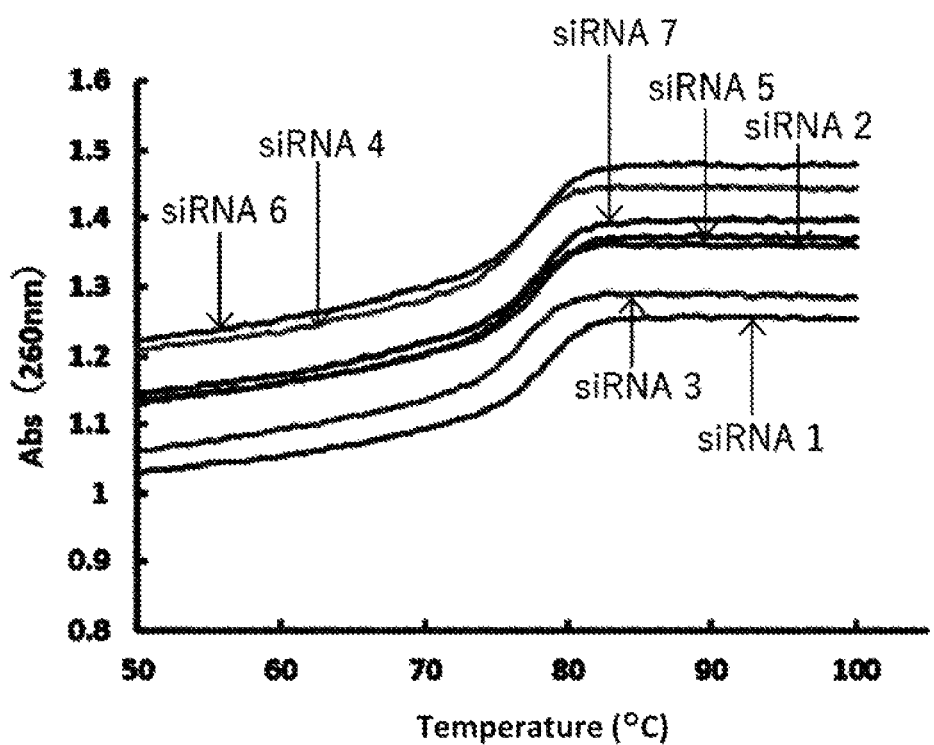
FIG. 2 is melting curves showing evaluation results of thermal stability of siRNAs 1 to 7 synthesized in Examples.

Hereinafter, preferable embodiments of the present invention are specifically described. However, the present invention should not be construed as being limited to these embodiments, and various changes, improvements, and the like may be made based on the knowledge of those skilled in the art as long as they do not depart from the spirit of the present invention. A plurality of components disclosed in the embodiments can form various inventions by appropriate combinations. For example, some components may be deleted from all components shown in the embodiments, and components of different embodiments may optionally be combined.

Nucleoside Derivative or Salt Thereof

A nucleoside derivative and a salt thereof according to an embodiment of the present invention have a basic substituent such as an aminoalkyl group bonded to 4' position of a sugar moiety (ribose or deoxyribose) via an oxygen atom. As used herein, the wording "nucleoside derivative" is a concept including a nucleotide derivative in which a phosphate is bound to the 5' position of the sugar moiety.

The introduction of the basic substituent such as the aminoalkyl group bonded via the oxygen atom into the 4' position of the sugar moiety allows the puckering of the sugar moiety to be controlled by stereoelectronic effects. Specifically, the group of the sugar moiety at the 4' position interacts with the group at the 2' position to suppress any bias from N-type to S-type, so that a ratio of the N-type sugar moiety present can be increased. Therefore, an oligonucleotide derivative having a structure derived from that nucleoside derivative, or a salt thereof (which may hereinafter be abbreviated as an "oligonucleotide derivative") can improve thermal stability of double-stranded nucleic acids such as double-stranded RNAs. Therefore, when the oligonucleotide derivative is used for siRNA, the thermal stability of the double-stranded RNA of siRNA can be improved, and a binding affinity to a target mRNA can be enhanced.

Further, since the nucleoside derivative according to an embodiment of the present invention has the basic substituent such as the aminoalkyl group bonded to the 4' position of the sugar moiety (ribose or deoxyribose) via the oxygen atom, an oligonucleotide derivative having a structure derived from that nucleoside derivative has a charge-adjusting ability that will neutralize at least a part of negative charges caused by the phosphate group or the like possessed by the oligonucleotide derivative.

The nucleoside derivative according to an embodiment of the present invention can be represented by the following formula (1). This nucleoside derivative will be a component of the oligonucleotide derivative and can be introduced into the structure of the oligonucleotide derivative by a method well known to a person skilled in the art. The nucleoside derivative can also improve the cell membrane permeability and ribonuclease resistance of the oligonucleotide derivative.

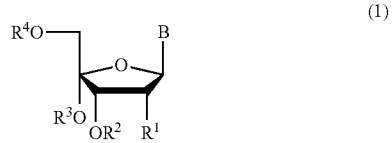
(1)

Regarding $R^1$ $R^1$ represents an alkoxy group, a hydrogen atom, or a halogen atom. When $R^1$ is the alkoxy group, the oligonucleotide derivative is a ribonucleotide derivative. When $R^1$ is the hydrogen atom or the halogen atom, the oligonucleotide derivative is a deoxyribonucleotide derivative.

Alkoxy Group

Non-limiting examples of the alkoxy group that can be used herein include saturated alkyl ether groups, which are linear, branched, cyclic, or combinations thereof.

The alkoxy group is preferably a lower alkoxy group. As used herein, the term "lower" means that the number of carbons forming the group is 10 or less, and preferably from 1 to 6, and more preferably from 1 to 5, and even more preferably from 1 to 4, and particularly preferably from 1 to 3.

The lower alkoxy group is preferably an alkoxy group having 1 to 4 carbon atoms, and more preferably an alkoxy group having 1 to 3 carbon atoms. Examples of the alkoxy group having 1 to 3 carbon atoms include methoxy, ethoxy, n-propoxy, cyclopropoxy, and cyclopropylmethoxy groups, and the like.

Halogen Atom

Non-limiting examples of the halogen atom that can be used herein include a chlorine atom, an iodine atom, a fluorine atom, a bromine atom and the like.

A downward bonding direction (α-position) of the halogen atom to the carbon atom at the 2' position of the ribose can increase a ratio of the N-type ribose present, so that the thermal stability of double-stranded nucleic acids such as double-stranded RNAs can further be improved by a synergistic effect with the substituent at the 4' position of the ribose. If the halogen atom is bonded upward (β-position), the ratio of the S-type ribose present tends to increase, and the effect of the substituent at the 4' position of the ribose results in a reduced effect of suppressing the bias toward S-type.

Regarding $R^2$ and $R^4$ $R^2$ and $R^4$, which may be the same as or different from each other, each represents a hydrogen atom, a protective group for a hydroxyl group, a phosphate group, a protected phosphate group, or —P(=O)$_n$R$^5$R$^6$ in which n represents 0 or 1, $R^5$ and $R^6$, which may be the same as or different from each other, each represents a hydrogen atom, a hydroxyl group, a protected hydroxyl group, a mercapto group, a protected mercapto group, an alkoxy group, a cyanoalkoxy group, an amino group, or a substituted amino group, provided that when n is 1, both $R^5$ and $R^6$ cannot be the hydrogen atom at the same time.

Protective Group for Hydroxy Group

The protective group for the hydroxyl group is well known in the art, and for examples, the protective groups described in Protective Groups in Organic Synthesis (John Wiley and Sons, 2007 Edition) can be used. Examples of the protective group for the hydroxyl group include an aliphatic acyl group; an aromatic acyl group; a lower alkoxymethyl group; an oxycarbonyl group optionally substituted; a tetrahydropyranyl group optionally substituted; a tetrathiopyranyl group optionally substituted; a methyl group substituted with a total of 1 to 3 substituted or unsubstituted aryl groups in which each substituent on each substituted aryl mean a lower alkyl, a lower alkoxy, a halogen atom, or a cyano group; a silyl group, and the like. Among them, the protective group for the hydroxyl group is preferably an aliphatic acyl group; an aromatic acyl group; a methyl group substituted with a total of 1 to 3 substituted or unsubstituted aryl groups in which the substituent on the substituted aryl is a lower alkyl, a lower alkoxy, a halogen atom or a cyano group; or a silyl group.

Examples of the aliphatic acyl group include alkylcarbonyl, carboxyalkylcarbonyl, halogenoalkylcarbonyl, and alkoxylated alkylcarbonyl groups.

Non-limiting examples of the alkyl groups forming the alkylcarbonyl, carboxyalkylcarbonyl, halogenoalkylcarbonyl and lower alkoxyalkylcarbonyl groups include saturated hydrocarbon groups which may be linear, branched, cyclic, or combination thereof. Further, the alkyl group is preferably a lower alkyl group. The lower alkyl group preferably has 1 to 6 carbon atoms, and more preferably 1 to 5 carbon atoms, and still more preferably 1 to 4 carbon atoms, and particularly preferably 1 to 3 carbon atoms. Examples of the linear lower alkyl group include methyl, ethyl, n-propyl, and n-butyl groups, and the like. Among them, the methyl group, the ethyl group or the n-propyl group is preferable, the methyl group or the ethyl group is more preferable, and the methyl group is further preferable. Examples of the branched alkyl group include isopropyl, isobutyl, s-butyl, and t-butyl groups, and the like. Among them, the isopropyl group is preferable. Examples of the cyclic alkyl group include cyclopropyl, cyclobutyl, and cyclopropylmethyl groups, and the like.

Specific examples of the alkylcarbonyl group include formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and henaicosyl groups, and the like. Among them, the acetyl group, the propionyl group, the butyryl group, the isobutyryl group, the pentanoyl group or the pivaloyl group is preferable, and the acetyl group is more preferable.

The position of the carboxy group forming the carboxyalkylcarbonyl group is not particularly limited and can be appropriately selected. Specific examples of carboxyalkylcarbonyl group include succinoyl, glutaroyl, and adipoyl groups.

The position of the halogen forming the halogenoalkylcarbonyl group is not particularly limited and can be appropriately selected. Specific examples of the halogenoalkylcarbonyl group include chloroacetyl, dichloroacetyl, trichloroacetyl, and trifluoroacetyl groups, and the like.

The position of the alkoxy group forming the alkylated alkylcarbonyl is not particularly limited and can be appropriately selected, Further, the alkoxy group can be selected to be the same as that of $R^1$. Specific examples of the alkoxylated alkylcarbonyl include a methoxyacetyl group and the like.

Examples of the aromatic acyl group include arylcarbonyl, halogenoarylcarbonyl, alkylated arylcarbonyl, alkoxylated arylcarbonyl, carboxylated arylcarbonyl, nitrated arylcarbonyl, and arylated arylcarbonyl groups, and the like.

Specific examples of the arylcarbonyl group include benzoyl, α-naphthoyl, and β-naphthoyl groups. Among them, the benzoyl group is preferred.

Specific examples of the halogenoarylcarbonyl group include 2-bromobenzoyl, and 4-chlorobenzoyl groups, and the like.

Specific examples of the alkylated arylcarbonyl group include 2,4,6-trimethylbenzoyl, 4-toluoyl, 3-toluoyl, and 2-toluoyl groups, and the like.

Specific examples of the alkoxylated arylcarbonyl group include 4-anisoyl, 3-anisoyl, and 2-anisoyl groups, and the like.

Specific examples of the carboxylated arylcarbonyl group include 2-carboxybenzoyl, 3-carboxybenzoyl, and 4-carboxybenzoyl groups, and the like.

Specific examples of the nitrated arylcarbonyl group include 4-nitrobenzoyl, 3-nitrobenzoyl, and 2-nitrobenzoyl groups, and the like.

Specific examples of the arylated arylcarbonyl group include 4-phenylbenzoyl group, and the like.

Examples of the lower alkoxymethyl group include methoxymethyl, 1,1-dimethyl-1-methoxymethyl, ethoxymethyl, propoxymethyl, isopropoxymethyl, butoxymethyl, and t-butoxymethyl groups, and the like. Among them, the methoxymethyl group is preferable.

Examples of the oxycarbonyl group optionally substituted include a lower alkoxycarbonyl group, a lower alkoxycarbonyl group substituted with a halogen or a silyl group, and an alkenyloxycarbonyl group, and the like.

Specific examples of the lower alkoxycarbonyl group include methoxycarbonyl, ethoxycarbonyl, t-butoxycarbonyl, isobutoxycarbonyl groups, and the like.

Specific examples of the lower alkoxycarbonyl group substituted with a halogen or a silyl group include 2,2-trichloroethoxycarbonyl, and 2-(trimethylsilyl)ethoxycarbonyl groups, and the like.

Specific examples of the alkenyloxycarbonyl group include a vinyloxycarbonyl group, and the like.

Examples of the tetrahydropyranyl group optionally substituted include tetrahydropyran-2-yl, and 3-bromotetrahydropyran-2-yl groups, and the like. Among them, the tetrahydropyran-2-yl group is preferable.

Examples of the tetrathiopyranyl group optionally substituted include tetrahydrothiopyran-2-yl, and 4-methoxytetrahydrothiopyran-4-yl groups, and the like. Among them, the tetrahydrothiopyran-2-yl group is preferable.

Examples of the methyl group substituted with a total of 1 to 3 substituted or unsubstituted aryl groups include benzyl, α-naphthylmethyl, β-naphthylmethyl, diphenylmethyl, triphenylmethyl, α-naphtyldiphenylmethyl, 9-anthrylmethyl-4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 4-chlorobenzyl, 4-bromobenzyl, and 4-cyanobenzyl groups, and the like. Among them, the benzyl group, the triphenylmethyl group, the 2,4,6-trimethylbenzyl group, the 3,4,5-trimethylbenzyl group, the 4-methoxybenzyl group, the 4-methoxyphenyldiphenylmethyl group or the 4,4'-dimethoxytriphenylmethyl group is preferred.

Examples of the silyl group include trimethylsilyl, triethylsilyl, isopropyldimethylsilyl, t-butyldimethylsilyl, methyldiisopropylsilyl, methyl-di-t-butylsilyl, triisopropylsilyl, diphenylmethylsilyl, diphenylbutyl silyl, and diphenylisopropylsilylphenyldiisopropylsilyl groups, and the like. Among them, the trimethylsilyl group, the t-butyldimethylsilyl group, the triisopropylsilyl group and the diphenylmethylsilyl group are preferable, and the trimethylsilyl group, the t-butyldimethylsilyl group or the diphenylmethylsilyl group is more preferable.

As used herein, the protective group for the hydroxyl group may also refer to a substituent that will be cleaved and released by either a chemical method (e.g., hydrogenolysis, hydrolysis, electrolysis, photolysis, or the like) or a biological method (e.g., hydrolysis in the human body, induction by microorganisms, or the like). In particular, the protective group for the hydroxyl group is preferably a substituent that will be released by hydrogenolysis or hydrolysis. Also, the protected hydroxyl group can also be the hydroxyl group in which the hydrogen atom is substituted with such a protective group.

Protected Phosphate Group

The protective group in the protected phosphate group is known in the art and can be appropriately selected with reference to the literatures as described above and descriptions thereof.

Examples of the protective group for the phosphate group include a lower alkyl group, a lower alkyl group substituted with a cyano group, an ethyl group substituted with a silyl group, a lower alkyl group substituted with a halogen, a lower alkenyl group, a lower alkenyl group substituted with a cyano group, a cycloalkyl group, an aralkyl group, an aralkyl group whose aryl ring is substituted with a nitro group, an aralkyl group whose aryl ring is substituted with halogen, an aryl group substituted with a lower alkyl group, an aryl group substituted with halogen, an aryl group substituted with a nitro group, and the like.

The lower alkyl group may employ those described above.

Specific examples of the lower alkyl group substituted with the cyano group include 2-cyanoethyl, and 2-cyano-1,1-dimethylethyl groups, and the like. Among them, the 2-cyanoethyl group is preferable.

Specific examples of the ethyl group substituted with the silyl group include 2-methyldiphenylsilylethyl, 2-trimethylsilylethyl, and 2-triphenylsilylethyl groups, and the like.

Specific examples of the lower alkyl group substituted with halogen include 2,2,2-trichloroethyl, 2,2,2-tribromoethyl, 2,2,2-trifluoroethyl, and 2,2,2-trichloroethyl groups, and the like. Among them, the 2,2,2-trichloroethyl group is preferable.

Specific examples of the lower alkenyl group include ethenyl, 1-propenyl, 2-propenyl, 1-methyl-2-propenyl, 1-methyl-1-propenyl, 2-methyl-1-propenyl, 1-butenyl, and 2-butenyl groups, and the like.

Specific examples of the lower alkenyl group substituted with the cyano group include 2-cyanoethyl, 2-cyanopropyl, and 2-cyanobutenyl groups, and the like.

Specific examples of the cycloalkyl group include cyclopropyl, cyclobutyl, cyclopentyl, and cyclohexyl groups, and the like.

Specific examples of the aralkyl group include benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, and 4-phenylbutyl groups, and the like. Among them, the benzyl group, the diphenylmethyl group, the triphenylmethyl group, the 1-phenethyl group or the 2-phenethyl group is preferable, and the benzyl group is more preferable.

Specific examples of the aralkyl group whose aryl ring is substituted with the nitro group include 2-(4-nitrophenyl)

ethyl, o-nitrobenzyl, 4-nitrobenzyl, 2,4-dinitrobenzyl, and 4-chloro-2-nitrobenzyl groups, and the like.

As used herein, the protective group for the phosphate group may also refer to a substituent that will be cleaved and released by either a chemical method (e.g., hydrogenolysis, hydrolysis, electrolysis, photolysis, or the like) or a biological method (e.g., hydrolysis in the human body, induction by microorganisms, or the like). In particular, the protective group for the phosphate group is preferably a substituent that will be released by hydrogenolysis or hydrolysis.

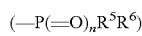

In the group —$P(=O)_n R^5 R^6$, n represents 0 or 1, $R^5$ and $R^6$, which may be the same as or different from each other, each represents a hydrogen atom, a hydroxyl group, a protected hydroxyl group, a mercapto group, a protected mercapto group, an alkoxy group, a cyanoalkoxy group, an amino group, or a substituted amino group, provided that when n is 1, both $R^5$ and $R^6$ cannot be the hydrogen atom at the same time.

As the protected hydroxyl group and alkoxy group, those described above can be used.

The protective group on the protected mercapto group is known in the art and can be appropriately selected with reference to the literatures as described above and descriptions thereof.

Examples of the protective group for the mercapto group include alkylthio, and arylthio groups, and the like, in addition to the groups illustrated as the protective group for the hydroxyl group (the aliphatic acyl group, the aromatic acyl group, and the like). Among them, the aliphatic acyl group or the aromatic acyl group is preferable, and the aromatic acyl group such as a benzoyl group is more preferable.

Examples of the alkylthio group include a saturated alkylthio group which is linear, branched, cyclic, or a combination thereof. Further, the alkyl group is preferably a lower alkylthio group. The lower alkylthio group preferably has 1 to 6 carbon atoms, and more preferably 1 to 5 carbon atoms, and still more preferably 1 to 4 carbon atoms, and particularly preferably 1 to 3 carbon atoms. Examples of alkylthio group having 1 to 4 carbon atoms include methylthio, ethylthio, n-propylthio, n-butylthio, isopropylthio, isobutylthio, s-butylthio, t-butylthio, cyclopropylthio, cyclobutylthio, and cyclopropylmethylthio groups, and the like. Among them, the methylthio group, the ethylthio group or the t-butylthio group are preferable.

Examples of the arylthio group include a benzylthio group and the like.

Examples of the cyanoalkoxy group include an alkoxy group substituted with a cyano group, which has 1 to 5 carbon atoms (when the carbon numbers are counted without including the number of carbon atoms in the cyano group) and which is linear, branched, cyclic, or a combination thereof. Specific examples of the cyanoalkoxy group include cyanomethoxy, 2-cyanoethoxy, 3-cyanopropoxy, 4-cyanobutoxy, 3-cyano-2-methylpropoxy, 1-cyanomethyl-1,1-dimethylmethoxy and the like. Among them, the 2-cyanoethoxy group is preferred.

Examples of the substituent of the substituted amino group that can be used herein include alkoxy, alkylthio, cyanoalkoxy, and alkyl groups, and the like. These groups may employ those described above.

Specific examples of —$P(=O)_n R^5 R^6$ include phosphoramidite, H-phosphonate and phosphonyl groups, and the like. Among them, the phosphoramidite group is preferable.

The group —$P(=O)_n R^5 R^6$ will be the phosphoramidite group when n is 0 and at least one of $R^5$ and $R^6$ is the substituted amino group. In particular, the phosphoramidite group in which one group of $R^5$ and $R^6$ is the substituted amino group and the other group is the alkoxy group or the cyanoalkoxy group is preferred, because it has an improved reaction efficiency of a condensation reaction. In this case, the substituted amino group is preferably a diethylamine group, a diisopropylamino group or a dimethylamino group, and more preferably the diisopropylamino group. The alkoxy group is preferably a methoxy group, and the cyanoalkoxy group is preferably a 2-cyanoethyl group. Specific examples of a particularly preferable phosphoramidite group include —$P(OC_2H_4CN)N(CH(CH_3)_2)$ or —$P(OCH_3)N(CH(CH_3)_2)$.

The group —$P(=O)_n R^5 R^6$ will be the H-phosphonate group when n is 1, one group of $R^5$ and $R^6$ is the hydrogen atom, and the other group is other than the hydrogen atom. In this case, the group other than the hydrogen atom is preferably a hydroxyl group, a methyl group, a methoxy group or a thiol group, and more preferably the hydroxyl group.

The group —$P(=O)_n R^5 R^6$ will be the phosphonyl group when n is 1 and both $R^5$ and $R^6$ are the alkoxy groups. In this case, the alkoxy groups may be the same as or different from each other. Further, the alkoxy group is preferably a methoxy group or an ethoxy group. Specific examples of the phosphonyl group include —$P(=O)(OCH_3)_2$.

Among the various groups as described above, $R^2$ is preferably the hydrogen atom, acetyl group, benzoyl group, benzyl group, p-methoxybenzyl group, trimethylsilyl group, tert-butyldiphenylsilyl group, —$P(OC_2H_4CN)N(CH(CH_3)_2)$, —$P(OCH_3)N(CH(CH_3)_2)$, or phosphonyl group. Further, $R^4$ is preferably the hydrogen atom, acetyl group, benzoyl group, benzyl group, p-methoxybenzyl group, dimethoxytrityl group, monomethoxytrityl group, tert-butyldiphenylsilyl group or trimethylsilyl group.

Regarding $R^3$

The group $R^3$ represents —$(CH_2)_m NHR^7$.

The symbol m represents an integer of 1 to 6. That is, the alkylene group represented by —$(CH_2)_m$ is a methylene group, an ethylene group, a propylene group, a butylene group, a pentylene group or a hexylene group. The symbol m is preferably an integer of 2 to 5, and more preferably an integer of 2 to 4, and even more preferably an integer of 2 to 3. That is, the alkylene group represented by —$(CH_2)_m$ is preferably an ethylene group, a propylene group, a butylene group or a pentylene group, and more preferably the ethylene group, the propylene group or the butylene group, and even more preferably the ethylene group or the propylene group. By selecting such an alkylene group, the nuclease resistance and cell membrane permeability of the oligonucleotide derivative can be improved.

The group $R^7$ represents a hydrogen atom, an alkyl group, an alkenyl group or a protective group for an amino group. Among these, the hydrogen atom is preferable.

As the alkyl group and the alkenyl group, those described above can be used.

Protective Group for Amino Group

The protective group for the amino group is well known in the art, and for examples, the protective groups described in Protective Groups in Organic Synthesis (John Wiley and Sons, 2007 Edition) can be used. Examples of the protective group for the amino group include, in addition to those listed above as the protective groups for the hydroxyl group, benzyl, methylbenzyl, chlorobenzyl, dichlorobenzyl, fluorobenzyl, trifluoromethylbenzyl, nitrobenzyl, methoxyphenyl, methoxymethyl (MOM), N-methylaminobenzyl, N,N-dimethylaminobenzyl, phenacyl, acetyl, trifluoroacetyl, pivaloyl, benzoyl, phthalimido, allyloxycarbonyl, 2,2,2-trichloroethoxycarbonyl, benzyloxycarbonyl, t-butoxycarbonyl (Boc), 1-methyl-1-(4-biphenypethoxycarbonyl (Bpoc), 9-fulolenylmethoxycarbonyl, benzyloxymethyl (BOM), and 2-(trimethylsilyl)ethoxymethyl (SEM) groups, and the like. Among them, the benzyl group, methoxyphenyl group, acetyl group, trifluoroacetyl (TFA) group, pivaloyl group, benzoyl group, t-butoxycarbonyl (Boc) group, 1-methyl-1-(4-biphenyl)ethoxycarbonyl (Bpoc) group, 9-fluorenylmethoxycarbonyl group, benzyloxymethyl (BOM) group, or 2-(trimethylsilyl)ethoxymethyl (SEM) group is preferable, and the benzyl group, methoxyphenyl group, acetyl group, benzoyl group, or benzyloxymethyl group is more preferable.

As used herein, the protective group for the amino group may also refer to a substituent that will be cleaved and released by either a chemical method (e.g., hydrogenolysis, hydrolysis, electrolysis, photolysis, or the like) or a biological method (e.g., hydrolysis in the human body, induction by microorganisms, or the like). In particular, the protective group for the amino group is preferably a substituent that will be released by hydrogenolysis or hydrolysis.

By selecting a substituent having the above structure as $R^3$, it is possible to provide the nucleoside derivative and an oligonucleotide derivative having a structure derived from the nucleoside derivative with a charge-imparting property having a characteristic that charges are changed in an ambient pH environment. For example, it can be cationic under acidic conditions, and the positive charge may decrease to zero under neutral physiological conditions. According to such an ability to adjust the charge, it is possible to dynamically change the charge of nucleoside derivative or impart the desired charge when necessary by changing the pH environment. Therefore, according to the nucleoside derivative having such a substituent, the charge of the oligonucleotide derivative can be adjusted in an unconventional manner or with an even higher degree of freedom than the prior arts. In view of the foregoing, the nucleoside derivative in which $R^3$ is a substituent having the structure as described above is useful as a charge (positive charge) imparting agent or a charge adjusting agent for oligonucleotide derivatives.

Regarding B

The symbol B (base) represents a purin-9-yl group, a 2-oxo-pyrimidin-1-yl group, a substituted purin-9-yl group, or a substituted 2-oxo-pyrimidin-1-yl group. The symbol B may be a natural base or an artificial base known in the art.

Specific examples of B include 2,6-dichloropurin-9-yl, 2-oxo-pyrimidin-1-yl, 2-oxo-4-methoxy-pyrimidin-1-yl, 4-(1H-1,2,4-triazol-1-yl)-pyrimidin-1-yl, 2,6-dimethoxypurin-9-yl, 2-oxo-4-amino-pyrimidin-1-yl with the amino group protected, 2-amino-6-bromopurin-9-yl with the amino group protected, 2-amino-6-hydroxypurin-9-yl with the amino group protected, 2-amino-6-hydroxypurin-9-yl with the amino group and/or the hydroxyl group protected, 2-amino-6-chloropurin-9-yl with the amino group protected, 6-aminopurin-9-yl with the amino group protected, 4-amino-5-methyl-2-oxo-pyrimidin-1-yl with the amino group protected, and the like. The protective groups for the hydroxyl group and the amino group may be as described above.

Other specific examples of B include 6-aminopurin-9-yl (adenine), 2-amino-6-hydroxypurin-9-yl (guanidine), 2-oxo-4-amino-pyrimidin-1-yl (cytosine), 2-oxo-4-hydroxy-pyrimidin-1-yl (uracil), 2-oxo-4-hydroxy-5-methylpyrimidin-1-yl (thymine), 4-amino-5-methyl-2-oxo-pyrimidin-1-yl (methylcytosine), 2,6-diaminopurin-9-yl, 6-amino-2-fluoropurin-9-yl, 6-mercaptopurin-9-yl, 4-amino-2-oxo-5-chloro-pyrimidin-1-yl, or 2-oxo-4-mercapto-pyrimidin-1-yl, 6-amino-2-methoxypurin-9-yl, 6-amino-2-chloropurin-9-yl, 2-amino-6-chloropurin-9-yl, 2-amino-6-bromopurin-9-yl, and the like.

The substituent on each of the substituted purin-9-yl group and the substituted 2-oxo-pyrimidin-1-yl group may be any one of a hydroxyl group, protected hydroxyl group, alkoxy group, mercapto group, protected mercapto group, alkylthio group, amino group, protected amino group, an amino group substituted with an alkyl group, alkyl group, alkoxymethyl group, triazole group or halogen atom, or combinations thereof. These substituents may be as described above.

Specific examples of the substituted purin-9-yl group include 6-aminopurin-9-yl, 2,6-diaminopurin-9-yl, 2-amino-6-chloropurin-9-yl, 2-amino-6-bromopurin-9-yl, 2-amino-6-hydroxypurin-9-yl, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, and the like. If there are amino groups or hydroxyl groups among the above substituents, preferred examples thereof include substituents in which those amino groups and/or hydroxyl groups are protected.

Specific examples of the substituted 2-oxo-pyrimidin-1-yl group include 2-oxo-4-amino-pyrimidin-1-yl, 1H-(1,2,4-triazol-1-yul)-pyrimidin-1-yl, 4-1H-1,4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl, 2-oxo-4-hydroxy-5-methylpyrimidin-1-yl, or 4-amino-5-methyl-2-oxo-pyrimidin-1-yl, and the like. Among them, 2-oxo-4-methoxy-pyrimidin-1-yl or 4-(1H-1,2,4-triazol-1-yl)-pyrimidin-1-yl is preferable.

If there are amino groups or hydroxyl groups in the substituents, they are preferably protected.

The nucleoside derivative according to the present invention may be in the form of a salt. The form of the salt is not particularly limited, but is generally an acid addition salt. The salt may also be in the form of an intramolecular counter ion, or depending on the type of substituent, it may also be in the form of a base addition salt.

The salt is preferably a pharmaceutically acceptable salt. Types of acids and bases that form the pharmaceutically acceptable salts are well known in the art, such as those described in J. Pharm. Sol., 1-19 (1977). For example, the acid addition salt includes salts of mineral acids and salts of organic acids. If one or more substituents contain an acidic moiety, it may be the base addition salt.

Examples of the salts of the mineral acids include hydrochloride salts, hydrobromide salts, hydroiodide salts, nitrate salts, sulfate salts, hydrosulfate salts, phosphate salts, hydrophosphate salts, and the like. Among them, the hydrochloride salts or the phosphate salts are preferable.

Examples of the salts of the organic acids include acetate salts, trifluoroacetate salts, gluconate salts, lactate salts, salicylate salts, citrate salts, tartrate salts, ascorbate salts, succinate salts, maleate salts, fumarate salts, formate salts, benzoate salts, methanesulfonate salts, ethanesulfonate salts, p-toluenesulfonate salts, and the like. Among them, the acetate salts are preferred.

Examples of the base addition salt include alkali metal salts, alkaline earth metal salts, organic amine salts, amino acid addition salts, and the like. Examples of the alkali metal salts include sodium, and potassium salts, and the like. Examples of the alkaline earth metal salts include magnesium and calcium salts. Examples of the organic amine salts include amino acid addition salts such as triethylamine, pyridine, procaine, picoline, dicyclohexylamine, diethanolamine, triethanolamine, and tris-(hydroxymethyl)aminomethane salts, and the like. Examples of the amino acid addition salts include arginine salts, lysine salts, ornithine salts, serine salts, glycine salts, asparaginate salts, glutamate salts, and the like.

The nucleoside derivative and salt thereof according to the embodiment of the present invention may exist as a hydrate or a solvate, and these substances are also included in the scope of the present specification. The nucleoside derivative or salt thereof can be easily produced by a person skilled in the art according to synthetic examples as described later or a known method.

The nucleoside derivative according to the embodiment of the present invention has a higher ratio of the N-type sugar moiety (ribose or deoxyribose) present, so that the introducing of the nucleoside derivative as at least a part of the oligonucleotide derivative can improve the thermal stability of double-stranded nucleic acids such as double-stranded RNAs. Therefore, when the oligonucleotide derivative is used for siRNA, the thermal stability of siRNA can be improved and the binding affinity to the target mRNA can be enhanced.

Further, the nucleoside derivative according to the embodiment of the present invention can improve the nuclease resistance of the single-stranded or double-stranded oligonucleotide derivative and can also improve the cell membrane permeability of mammalian cells and the like. That is, the nucleoside derivative itself is useful as a nuclease resistance enhancer and/or a cell membrane permeability-imparting agent. Further, the nucleoside derivative can provide an oligonucleotide derivative suitable for administration without using a carrier such as LNP for delivery, which has been used for conventional nucleic acid medicines.

Furthermore, since the nucleoside derivative according to the embodiment of the present invention has the basic substituent at the 4' position of the sugar moiety, it can function as a charge adjusting agent or positive charge imparting agent that can adjust a negative charge derived from the phosphate group or the like on the oligonucleotide derivative.

Oligonucleotide Derivative and Salt Thereof

The oligonucleotide derivative or salt thereof (which may hereinafter be abbreviated as an "oligonucleotide derivative") according to an embodiment of the present invention includes at least one partial structure represented by the following formula (2). The partial structure can be obtained from the nucleoside derivative represented by the above formula (1) and the salt thereof.

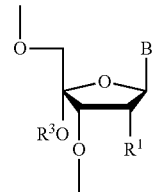

(2)

In the formula (2), $R^1$, $R^2$ and B are the same as those defined in the formula (1). That is, $R^1$ represents an alkoxy group, a hydrogen atom, or a halogen atom; $R^3$ represents $-(CH_2)_m NHR^7$ in which m represents an integer of 1 to 6, and $R^7$ represents a hydrogen atom, an alkyl group, an alkenyl group, or a protective group for an amino group; and B represents a purin-9-yl group, a 2-oxo-pyrimidin-1-yl group, a substituted purin-9-yl group, or a substituted 2-oxo-pyrimidin-1-yl group.

One or two or more partial structures represented by the formula (2) may be included in the oligonucleotide derivative. When a plurality of partial structures represented by formula (2) are included, these partial structures may be the same as or different from each other. Also, the entire partial structure included in the oligonucleotide derivative may be comprised only of the partial structure represented by the formula (2). By having a plurality of partial structures represented by the formula (2), the cell membrane permeability and ribonuclease resistance can be reliably improved.

The position of the partial structure represented by the formula (2) in the oligonucleotide derivative is not particularly limited, but it can be on either or both of the 5' end side and the 3' end side, for example. As used herein, each of the 5' end side and the 3' end side refers to a region in a range of an appropriate number of units from each end of a polymer chain of the oligonucleotide derivative. For example, it refers to a region comprised of no more than 30% of the total constituent unit of the polymer chain. A percentage of the above range from the end can generally be 25% or less (e.g., 20% or less, 10% or less, 5% or less, etc.), although it may vary depending on the total length of the polymer chain. More specifically, each of the 5' end side and the 3' end side can typically be a region of 1 to 30 constituent units (e.g., 1 to 25, 1 to 20, 1 to 15, 1 to 10, 1 to 8, 1 to 6, 1 to 5, 1 to 4, 1 to 3, or 1 to 2 units, etc.) from each end. The oligonucleotide derivative can include one, or two or more partial structures represented by the formula (2) in any of those end regions. For example, the oligonucleotide derivative can include the partial structure(s) represented by the formula (2) at either or both of the first constituent units from the 5' end and the 3' end.

In the oligonucleotide derivative according to an embodiment of the present invention, one or more partial structures represented by the formula (2) can be included in the central portion which is a portion other than the 5' end side and the 3' end side. Arranging the partial structure represented by the formula (2) in the central portion can lead to easier improvement and adjustment of the ribonuclease resistance and cell membrane permeability, and also lead to easier adjustment of the overall charge of the oligonucleotide. Such an arrangement can also lead to easier adjustment of the overall charge of the oligonucleotide.

The oligonucleotide derivative according to the embodiment of the present invention may also include the partial structures represented by the formula (2) on either or both of the 5' end side and the 3'end side and in the central portion.

For example, the oligonucleotide derivative according to the embodiment of the present invention can include one or more partial structures represented by the formula (2) on the 5' end side, on the 3' end side and in the central portion, respectively.

When the oligonucleotide derivative includes two or more partial structures represented by the formula (2), the arrangement of the partial structures is not particularly limited, and the partial structures may be adjacent to each other or may exist apart from each other. For example, when the oligonucleotide derivative includes three partial structures represented by the formula (2), each partial structure may be substantially equally arranged on each of the 5' end side, the center, and the 3' end side of the oligonucleotide derivative. As used herein, the phrase "each partial structure may be substantially equally arranged on each of . . . " is not limited to arranging the partial structures with the same number on each part of the oligonucleotide derivative, but it means that at least one partial structure is arranged on each part of the oligonucleotide derivative. For example, if one to three partial structures are arranged on each part of the oligonucleotide derivative, it can be "substantially equally". At least six partial structures may be included in the oligonucleotide derivative.

As described above, the partial structures represented by the formula (2) may be substantially equally or dispersedly arranged as a whole, thereby improving a charge adjusting property in addition to ribonuclease resistance and cell membrane permeability. From the viewpoint of the effect of improving these properties, it is preferable that two or more partial structures represented by the formula (2) are arranged in the center of the oligonucleotide derivative.

Since the sugar moiety of the partial structure represented by the formula (2) is derived from ribose or deoxyribose, the oligonucleotide derivative is an oligoribonucleotide derivative, an oligodeoxyribonucleotide derivative, or a chimera of a ribonucleotide derivative and a deoxyribonucleotide derivative.

The oligonucleotide derivative itself according to the embodiment of the present invention is in the form of a single strand, but it may also be in the form of a hybrid, or double strand, of two of: an oligoribonucleotide derivative, an oligodeoxyribonucleotide derivative, and an oligodeoxyribonucleotide derivativeiribonucleotide derivative (chimeric strand).

The oligonucleotide derivative according to the embodiment of the present invention may include a partial structure(s) other than the partial structure represented by the formula (2) (hereinafter referred to as "other partial structure"). The other partial structures include natural or known nucleotide derivatives and partial structures corresponding to the nucleotide derivatives. The partial structure represented by the formula (2) and the other partial structure can be bonded to each other by, for example, a phosphodiester bond, a phosphomonoester bond, a phosphorothioate bond, or the like.

The oligonucleotide derivative according to an embodiment of the present invention has the total number of the partial structures represented by formula (2) and the other substructures of, preferably 2 or more, and more preferably 8 or more, and even more preferably 15 or more. On the other hand, the upper limit of the total number of these partial structures is not particularly limited, but the total number may generally be 100 or less (e.g., 80 or less, 60 or less, 50 or less, 40 or less, 30 or less, or 20 or less).

The oligonucleotide derivative according to the embodiment of the present invention may have one or more asymmetric centers or stereoisomers in the other partial structure, and any mixture of stereoisomers or racemates are also included in the scope of the present invention. Also, the presence of tautomers is also included in the scope of the present invention.

The oligonucleotide derivative according to the embodiment of the present invention can be used as an alternative to ribonucleotide derivatives by including uracil (U) or the like, a base in RNA, or the like as the base of B in the partial structure represented by the formula (2).

The oligonucleotide derivative according to the embodiment of the present invention may be in the form of a salt. Although the form of the salt is not particularly limited, it is preferably a pharmaceutically acceptable salt. For the salt, the forms of the salts in the nucleoside derivative as described above may be applied.

The oligonucleotide derivative and salt thereof according to the embodiment of the present invention may be in the form of a hydrate or solvate, which is also included in the scope of the present invention.

The oligonucleotide derivative according to the embodiment of the present invention has a higher ratio of the N-type sugar moiety (ribose or deoxyribose) present, which can improve the thermal stability of double-stranded nucleic acids such as double-stranded RNAs. Therefore, the oligonucleotide derivative can be used for siRNA. The use of the oligonucleotide derivative for siRNA can improve the thermal stability of siRNA and enhance the binding affinity to the target mRNA. Therefore, the target mRNA can be efficiently degraded and the information on the target mRNA can be prevented from being translated into specific proteins by the ribosome.

Since the oligonucleotide derivative according to the embodiment of the present invention has a certain N-containing group via oxygen at the 4' position of the sugar moiety (ribose or deoxyribose), it can adjust a substantial charge amount of RNA while maintaining RNA functions in living organisms, such as RNA interference ability. Further, since the oligonucleotide derivative can enhance lipophilicity (van der Waals intermolecular force), and reduce the degree of decrease in a melting temperature of dsRNA, it is possible to inhibit the decrease in the thermal stability. Therefore, the oligonucleotide derivative can improve ribonuclease resistance and cell membrane permeability. Further, since the oligonucleotide derivative according to the embodiment of the present invention has the basic substituent at the 4' position of the sugar moiety, it can also neutralize the negative charge caused by the phosphate groups and the like, and regulate the overall charge.

Therefore, the oligonucleotide derivative according to the embodiment of the present invention can be incorporated as a constituent of miRNA or as a constituent of aptamer RNA, and can be utilized while taking advantage of the effects of improving the ribonuclease resistance and cell membrane permeability. Further, the oligonucleotide derivatives according to the embodiments of the present invention can be linked to other compounds to form conjugates. Furthermore, the oligonucleotide derivatives according to the embodiments of the present invention can be used as components of ribozymes, RNA chips, and other reagents.

In view of the foregoing, the oligonucleotide derivatives according to the embodiments of the present invention are expected to be more useful than natural nucleotides as components of various nucleic acid drugs, such as anti-tumor drugs and anti-viral drugs, which treat diseases by inhibiting the function of genes, by taking advantage of features that are not found in the natural nucleotides. The nucleic acid drugs include siRNAs, antisense nucleic acids, miRNAs, aptamers, decoys, and the like. The oligonucleotide derivatives according to the embodiments of the present invention are also useful as raw materials or intermediates for the nucleic acid drugs.

The charge adjusting property, ribonuclease resistance, cell membrane permeability, and charge adjusting ability of the oligonucleotide derivatives, as well as the biological activity of various RNAs including these oligonucleotide derivatives, can be easily evaluated by a person skilled in the art, as appropriate, by referring to Examples described below and the methods well known in the art at the time of filing this application.

Production of Nucleoside Derivative and Oligonucleotide Derivative

The nucleoside derivatives and the oligonucleotide derivatives according to the embodiments of the present invention can be easily synthesized by a person skilled in the art based on specific synthetic examples as described below or synthetic techniques for nucleoside derivatives and oligonucleotide derivatives known in the art at the time of the filing of this application. For example, a synthesis scheme for the nucleoside derivative can be designed based on the descriptions: Bioorganic & Medical Chemistry 11 (2003) 211-2226; Bioorganic & Chemistry letters (1999) 2667-2672; The Journal of Organic Chemistry 2013, 78, 9956-9962; HELVATICA CHIMICA ACTA Vol. 83 (2000) 128-151; Bioorganic & Medical Chemistry 11 (2003) 211-2226; Bioorganic & Chemistry letters (1999) 2667-2672, and the like.

The oligonucleotide derivative having the partial structure(s) represented by the formula (2) can be easily produced by using the nucleoside derivative represented by the formula (1) as an amidite agent. In other words, the oligonucleotide derivative having the partial structure(s) represented by the formula (2) can be synthesized by using the nucleoside derivative represented by the formula (1) with a known DNA synthesizer. The oligonucleotide derivative thus obtained may be purified using a column, and the purity of the product may be measured by reversed-phase HPLC or MALDI-TOF-MS. In addition, the method of converting the oligonucleotide derivative to the acid addition salt is well known in the art.

EXAMPLES

The embodiments of the invention are described in more detail by means of Examples below, but the present invention is not limited in any way by these Examples.

Synthesis of Nucleoside Derivative (Amidite)

(1) 2'-OMe-4'-aminoethoxyuridine

According to the following scheme, using uridine (compound 1) as a starting material, 5'-O-[bis(4-methoxyphenyl)phenylmethyl]-4'-C-trifluoroacetylaminoethoxyl-2'-O-methyl-3'-[2-cyanoethyl-N,N-bis(1-methylethyl)-phosphoroamidite]-uridine (compound 12) was synthesized.

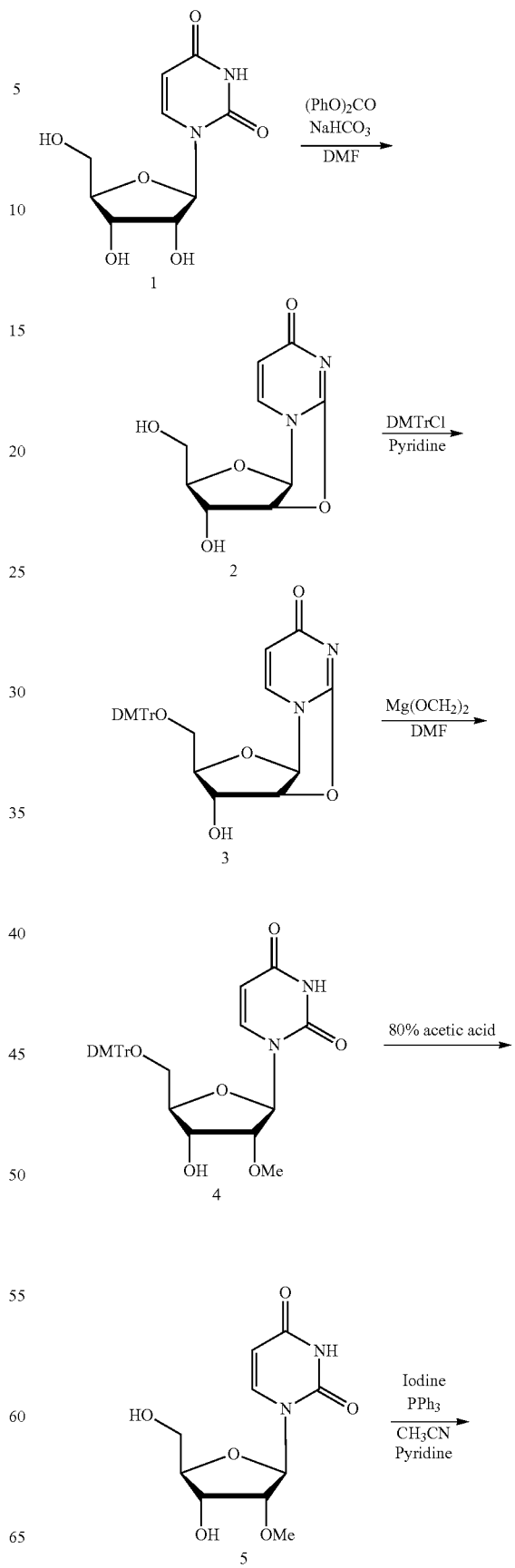

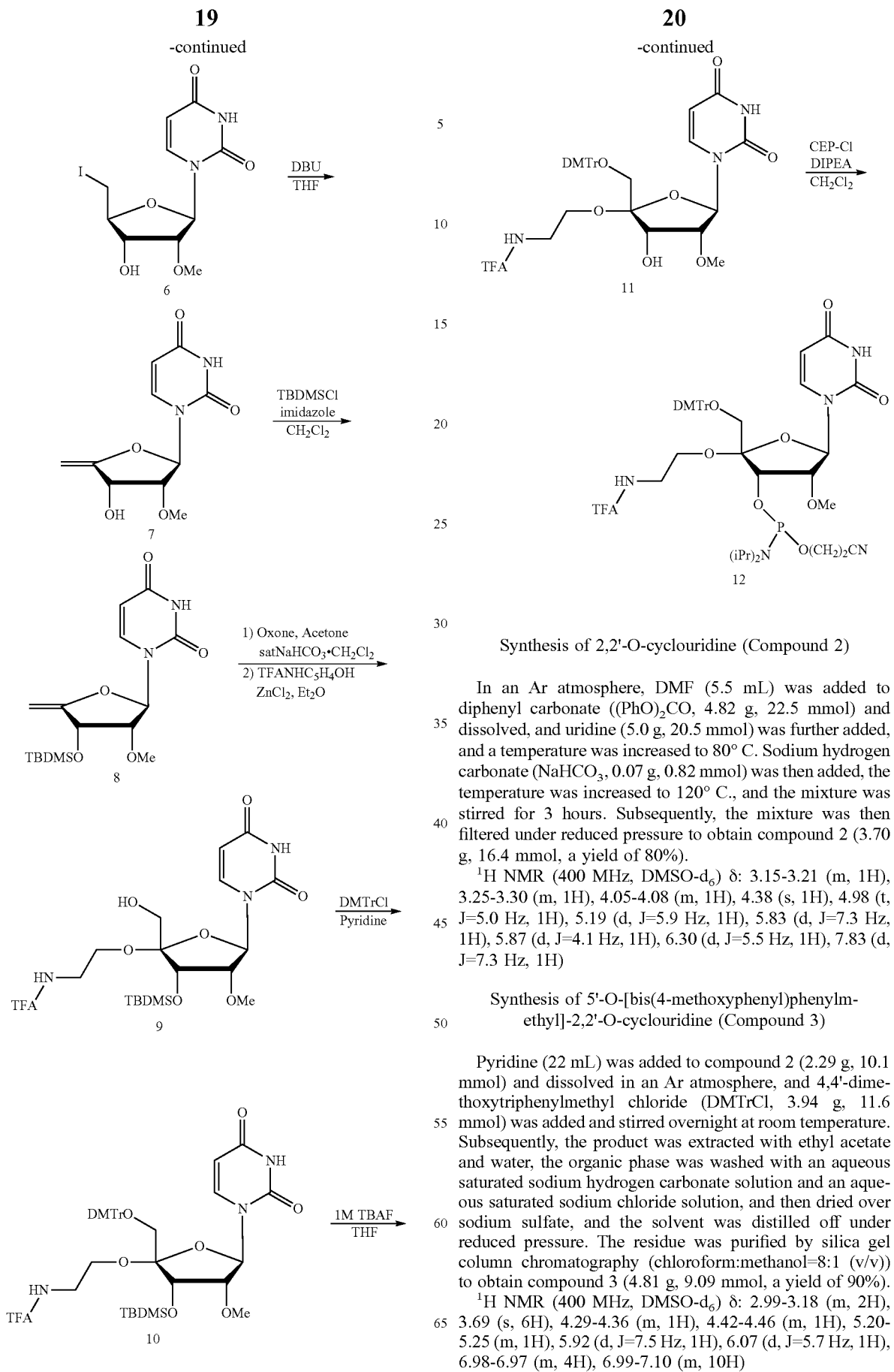

Synthesis of 2,2'-O-cyclouridine (Compound 2)

In an Ar atmosphere, DMF (5.5 mL) was added to diphenyl carbonate ((PhO)$_2$CO, 4.82 g, 22.5 mmol) and dissolved, and uridine (5.0 g, 20.5 mmol) was further added, and a temperature was increased to 80° C. Sodium hydrogen carbonate (NaHCO$_3$, 0.07 g, 0.82 mmol) was then added, the temperature was increased to 120° C., and the mixture was stirred for 3 hours. Subsequently, the mixture was then filtered under reduced pressure to obtain compound 2 (3.70 g, 16.4 mmol, a yield of 80%).

$^1$H NMR (400 MHz, DMSO-d$_6$) δ: 3.15-3.21 (m, 1H), 3.25-3.30 (m, 1H), 4.05-4.08 (m, 1H), 4.38 (s, 1H), 4.98 (t, J=5.0 Hz, 1H), 5.19 (d, J=5.9 Hz, 1H), 5.83 (d, J=7.3 Hz, 1H), 5.87 (d, J=4.1 Hz, 1H), 6.30 (d, J=5.5 Hz, 1H), 7.83 (d, J=7.3 Hz, 1H)

Synthesis of 5'-O-[bis(4-methoxyphenyl)phenylmethyl]-2,2'-O-cyclouridine (Compound 3)

Pyridine (22 mL) was added to compound 2 (2.29 g, 10.1 mmol) and dissolved in an Ar atmosphere, and 4,4'-dimethoxytriphenylmethyl chloride (DMTrCl, 3.94 g, 11.6 mmol) was added and stirred overnight at room temperature. Subsequently, the product was extracted with ethyl acetate and water, the organic phase was washed with an aqueous saturated sodium hydrogen carbonate solution and an aqueous saturated sodium chloride solution, and then dried over sodium sulfate, and the solvent was distilled off under reduced pressure. The residue was purified by silica gel column chromatography (chloroform:methanol=8:1 (v/v)) to obtain compound 3 (4.81 g, 9.09 mmol, a yield of 90%).

$^1$H NMR (400 MHz, DMSO-d$_6$) δ: 2.99-3.18 (m, 2H), 3.69 (s, 6H), 4.29-4.36 (m, 1H), 4.42-4.46 (m, 1H), 5.20-5.25 (m, 1H), 5.92 (d, J=7.5 Hz, 1H), 6.07 (d, J=5.7 Hz, 1H), 6.98-6.97 (m, 4H), 6.99-7.10 (m, 10H)

Synthesis of 5'-O-[bis(4-methoxyphenyl)phenylmethyl]-2'-O-methyl (Compound 4)

DMF (100 mL) was added to compound 3 (6.76 g, 12.8 mmol) and dissolved in an Ar atmosphere, and Mg(OCH$_3$)$_2$ (6.62 g, 76.7 mmol) was added and stirred at 100° C. for 2 hours. The product was then extracted with ethyl acetate and an aqueous saturated sodium hydrogen carbonate solution, the organic phase was washed with an aqueous saturated sodium hydrogen carbonate solution and an aqueous saturated sodium chloride solution, and then dried over sodium sulfate, and the solvent was distilled off under reduced pressure. The residue was purified by silica gel column chromatography (hexane:ethyl acetate=1:5 (v/v)) to obtain compound 4 (5.43 g, 9.67 mmol, a yield of 76%).

$^1$H NMR (500 MHz, CDCl$_3$) δ: 2.57 (d, J=9.2 Hz, 1H), 3.51-3.59 (m. 2H), 3.65 (s, 3H), 3.80 (s, 8H), 4.49 (d, J=8.0 Hz, 1H), 4.46-4.49 (m, 1H), 5.25 (dd, J=2.3, 8.1 Hz, 1H), 5.96 (s, 1H), 6.84 (d, J=8.6 Hz, 4H), 7.24 (s, 1H), 7.26-7.34 (m, 6H), 7.38 (d, J=7.5 Hz, 2H), 8.05 (d, J=8.0 Hz, 1H), 8.44 (s, 1H)

Synthesis of 2'-O-methyl-uridine (Compound 5)

In an Ar atmosphere, 80% acetic acid (50 mL) was added to compound 4 (2.94 g, 5.25 mmol), dissolved, and stirred at room temperature for 1 hour, and the solvent was then distilled off under reduced pressure. The residue was purified by silica gel column chromatography (chloroform:methanol=1:5 (v/v)) to obtain compound 5 (1.22 g, 4.71 mmol, a yield of 90%).

$^1$H NMR (400 MHz, DMSO-d$_6$) δ: 3.52 (s, 1H), 3.46-3.53 (m, 1H), 3.60-3.65 (m, 1H), 3.78 (t, J=5.0 Hz, 1H), 3.85 (dd, J=3.2, 8.0 Hz, 1H) 4.11 (dd, J=5.0, 10.5 Hz, 1H), 5.16 (s, 1H), 5.17 (s, 1H), 5.65 (d, J=8.2 Hz, 1H), 5.85 (d, J=5.0, 1H), 7.93 (d, J=8.2 Hz, 1H), 11.4 (s, 1H)

Synthesis of 5'-iodo-2'-deoxy-2'-O-methyl-uridine (Compound 6)

Acetonitrile (CH$_3$CN, 68 mL) was added to compound 5 (0.93 g, 3.61 mmol) and dissolved in an Ar atmosphere, and pyridine (3.75 mL), iodine (1.09 g, 4.33 mmol), and triphenylphosphine (PPh$_3$, 1.23 g, 4.69 mmol) were added and stirred at room temperature for 72 hours, and the solvent was then distilled off under reduced pressure. The residue was purified by silica gel column chromatography (chloroform:methanol=10:1 (v/v)) to obtain compound 6 (1.22 g, 3.49 mmol, a yield of 97%).

$^1$H NMR (500 MHz, CDCl$_3$) δ: 3.46 (dd, J=4.6, 11.5 Hz, 1H), 3.60 (s, 3H), 3.63 (d, J=3.4 Hz, 1H), 3.69-3.72 (m, 1H), 3.85 (dd, J=2.9, 6.3 Hz, 1H), 5.79 (dd, J=2.3, 8.0 Hz, 1H), 5.91 (d, J=2.9 Hz, 1H), 7.45-7.48 (m, 1H), 7.67 (d, J=8.0 Hz, 2H), 8.90 (s, 1H)

Synthesis of 4',5'-didehydro-2', 5'-dideoxy-2'-O-methyl-uridine (Compound 7)

In an Ar atmosphere, THF (20 mL) was added to compound 6 (1.29 g, 3.49 mmol) and dissolved, and DBU (3.12 mL, 20.9 mmol) was added and stirred overnight at room temperature, and the solvent was then distilled off under reduced pressure. The residue was purified by silica gel column chromatography (chloroform:methanol=10:1 (v/v)) to obtain compound 7 (0.47 g, 1.96 mmol, a yield of 56%).

$^1$H NMR (500 MHz, CDCl$_3$) δ: 3.15 (s, 1H), 3.59 (s, 3H), 3.88 (dd, J=1.2, 5.5 Hz, 1H), 4.46 (t, J=2.0 Hz, 1H), 4.57 (s, 1H), 4.65 (t, J=2.0 Hz, 1H), 5.78 (d, J=8.1 Hz, 1H), 6.02 (s, 1H), 7.17 (d, J=8.6 Hz, 1H), 5.91 (d, J=2.9 Hz, 1H), 7.45-7.48 (m, 1H), 7.67 (d, J=8.0 Hz, 2H), 8.90 (s, 1H)

Synthesis of 4',5'-didehydro-2',5'-dideoxy-3'-O-[(1,1-dimethylethyl)diphenylsilyl]-2'-O-methyl-uridine (Compound 8)

Dichloromethane (CH$_2$Cl$_2$, 5 mL) was added to compound 7 (0.47 g, 1.96 mmol) and dissolved in an Ar atmosphere, and tert-butyldimethylchlorosilane (TBDMSCI, 0.55 g, 3.65 mmol) and imidazole (0.34 g, 4.9 mmol) were added and stirred at room temperature for 3 hours, and ethanol was then added to quench it. The product was then extracted with ethyl acetate and an aqueous saturated sodium hydrogen carbonate solution, the organic phase was washed with an aqueous saturated sodium hydrogen carbonate solution and an aqueous saturated sodium chloride solution, and then dried over sodium sulfate, and the solvent was distilled off under reduced pressure. The residue was purified by silica gel column chromatography (hexane:ethyl acetate=2:1 (v/v)) to obtain compound 8 (0.57 g, 1.60 mmol, a yield of 81%).

$^1$H NMR (400 MHz, CDCl$_3$) δ: 0.14 (s, 6H), 0.93 (s, 9H), 3.51 (s, 1H), 3.79-3.81 (m, 1H), 4.33-4.44 (m, 1H), 4.56-4.58 (m, 1H), 4.61-4.62 (m, 1H), 5.78 (dd, =2.3, 8.2 Hz, 1H), 6.08 (d, J=3.6 Hz, 1H), 7.18 (d, J=8.2 Hz, 1H), 8.59 (s, 1H)

Synthesis of 4'-C-trifluoroacetylaminoethoxyl-3'-O-[(1,1-dimethylethyl)diphenylsilyl]-2'-O-methyl (Compound 9)

Dichloromethane (CH$_2$Cl$_2$, 2.8 mL) was added to compound 8 (0.14 g, 0.40 mmol) and dissolved in an Ar atmosphere, and acetone (2.8 mL) and an aqueous saturated sodium hydrogen carbonate solution (2.8 mL) were added, an aqueous solution (2.8 mL) of Oxone (0.18 g, 1.20 mmol) was added at 0° C., and stirred at room temperature for 3 hours. The product was then extracted with chloroform and an aqueous saturated sodium hydrogen carbonate solution, the organic phase was washed with an aqueous saturated sodium hydrogen carbonate solution and an aqueous saturated sodium chloride solution, and then dried over sodium sulfate, and the solvent was distilled off under reduced pressure to obtain a crude product. Subsequently, diethyl ether (3 mL) was added to the crude product and dissolved in an Ar atmosphere, and 1.0 M zinc chloride (0.48 mmol, 0.48 mL), and [2-(2,2,2-trifluoroacetamide)ethoxy]methyl acetate (0.63 g, 4.0 mmol) were added at −40° C., stirred at room temperature for 12 hours, and then quenched with an aqueous saturated sodium hydrogen carbonate solution, and filtered through Celite. The product was extracted from the filtrate with ethyl acetate and an aqueous saturated sodium hydrogen carbonate solution, and the organic phase was washed with water and an aqueous saturated sodium chloride solution, and then dried over sodium sulfate, and the solvent was distilled off under reduced pressure. The residue was purified by silica gel column chromatography (hexane:ethyl acetate=1:1 (v/v)) to obtain compound 9 (0.15 g, 0.28 mmol, a yield of 69%).

$^1$H NMR (500 MHz, DMSO-d$_6$) δ: 0.10 (d, J=13.1, 6H), 0.89 (s, 1H), 3.3 (s, 3H) 3.42-3.46 (m, 1H), 3.49-3.53 (m, 1H), 3.69-3.73 (m, 2H), 3.91 (t, J=5.7, 1H), 4.42 (d, J=6.3 Hz, 1H), 5.39 (t, J=5.5 Hz, 1H), 5.70 (dd, J=8, 1.8 Hz, 1H), 6.06 (d, J=5.7 Hz, 1H), 7.82 (d, J=8.0 Hz, 1H), 9.21 (t, J=5.1 Hz, 1H), 11.4 (s, 1H)

Synthesis of 5'-O-[bis(4-methoxyphenyl)phenylmethyl]-4'-C-trifluoroacetylaminoethoxyl-3'-O-[(1,1-dimethylethyl)diphenylsilyl]-2'-O-methyl-uridine (Compound 10)

Pyridine (3 mL) was added to compound 9 (0.25 g, 0.48 mmol) and dissolved in an Ar atmosphere, and 4,4'-dimethoxytriphenylmethyl chloride (DMTrCl, 0.25 g, 0.72 mmol) was added and stirred overnight at room temperature. The product was then extracted with chloroform and an aqueous saturated sodium hydrogen carbonate solution, and the organic phase was washed with an aqueous saturated sodium hydrogen carbonate solution and an aqueous saturated sodium chloride solution, and then dried over sodium sulfate, and the solvent was distilled off under reduced pressure. The residue was purified by silica gel column chromatography (chloroform:methanol=3:1 (v/v)) to obtain compound 10 (0.35 g, 0.42 mmol, a yield of 89%).

$^1$H NMR (500 MHz, CDCl$_3$) δ: 0.01 (s, 6H), 0.81 (s, 9H), 3.17 (d, J=5.15 Hz, 6H), 3.30 (s, 3H), 3.56-3.58 (m, 1H), 3.66-3.74 (m, 1H), 3.90 (dd, J=6.3, 3.4 Hz, 1H), 4.45 (d, J=6.3 Hz, 1H), 5.28 (d, J=8.0 Hz, 1H), 5.97 (d, J=3.4 Hz, 1H), 6.90 (dd, J=6.9, 1.8 Hz, 4H), 7.21-7.24 (m, 5H), 7.32-7.35 (m, 4H), 7.77 (d, J=8.6 Hz, 1H), 9.11 (t, J=5.5 Hz, 1H), 11.5 (s, 1H)

Synthesis of 5'-O-[bis(4-methoxyphenyl)phenylmethyl]-4'-C-trifluoroacetylaminoethoxyl-2'-O-methyl-uridine (Compound 11)

In an Ar atmosphere, THF (1.47 mL) was added to compound 10 (0.25 g, 0.30 mmol) and dissolved, and 1 M tetrabutylammonium fluoride (TBAF, 0.47 mL) was added and stirred at room temperature for 3 hours. The solvent was then distilled off under reduced pressure. The residue was purified by silica gel column chromatography (hexane:ethyl acetate=1:1 (v/v)) to obtain compound 11 (0.21 g, 0.29 mmol, 97%).

$^1$H NMR (500M Hz, CDCl$_3$) δ: 2.84 (d, J=12.0 Hz, 1H), 3.24 (dd, J=10.3, 13.8 Hz, 1H), 3.45-3.51 (m, 3H), 3.65 (s, 3H), 3.74 (d, J=6.3 Hz, 2H), 3.8 (s, 5H), 4.63 (dd, J=6.9, 5.9 Hz, 1H), 5.17 (d, J=8.6 Hz, 1H), 5.93 (s, 1H), 6.85 (d, J=9.2 Hz, 4H), 7.13 (s, 1H), 7.23-7.27 (m, 4H), 7.29-7.35 (m, 5H), 7.93 (d, J=3.5 Hz, 1H), 8.26 (s, 1H)

Synthesis of 5'-O-[bis(4-methoxyphenyl)phenylmethyl]-4'-C-trifluoroacetylaminoethoxyl-2'-O-methyl-3'-[2-cyanoethyl-N,N-bis(1-methylethyl)-phosphoramidite]-uridine (Compound 12)

In an Ar atmosphere, chloroform (2.7 mL) was added to compound 11 (0.27 g, 0.38 mmol) and dissolved, and N,N-diisopropylethylamine (DIPEA, 0.33 mL, 1.905 mmol), and 2-cyanoethyl-N,N-diisopropylchlorophosphoramidite (CEP-Cl, 0.17 mL, 0.76 mmol) were added, and stirred at room temperature for 1 hour. The product was extracted with chloroform and an aqueous saturated sodium hydrogen carbonate solution, washed with an aqueous saturated sodium chloride solution, and then dried over sodium sulfate, and the solvent was distilled off under reduced pressure. The residue was purified by silica gel column chromatography (hexane:ethyl acetate=2:3 (v/v)) to obtain compound 12 (0.14 g, 0.15 mmol, a yield of 40%). $^{31}$P NMR (162 MHz, CDCl$_3$) δ: 151.59, 151.80

(2) 2'-OMe-4'-aminopropoxyuridine

According to the following scheme, using the uridine (compound 8) obtained above, 5'-O-[bis(4-methoxyphenyl)phenylmethyl]-4'-C-trifluoroacetylaminopropoxyl-2'-O-methyl-3'-[2-cyanoethyl-N,N-bis(1-methylethyl)-phosphoroamidite]-uridine (compound 16) was synthesized.

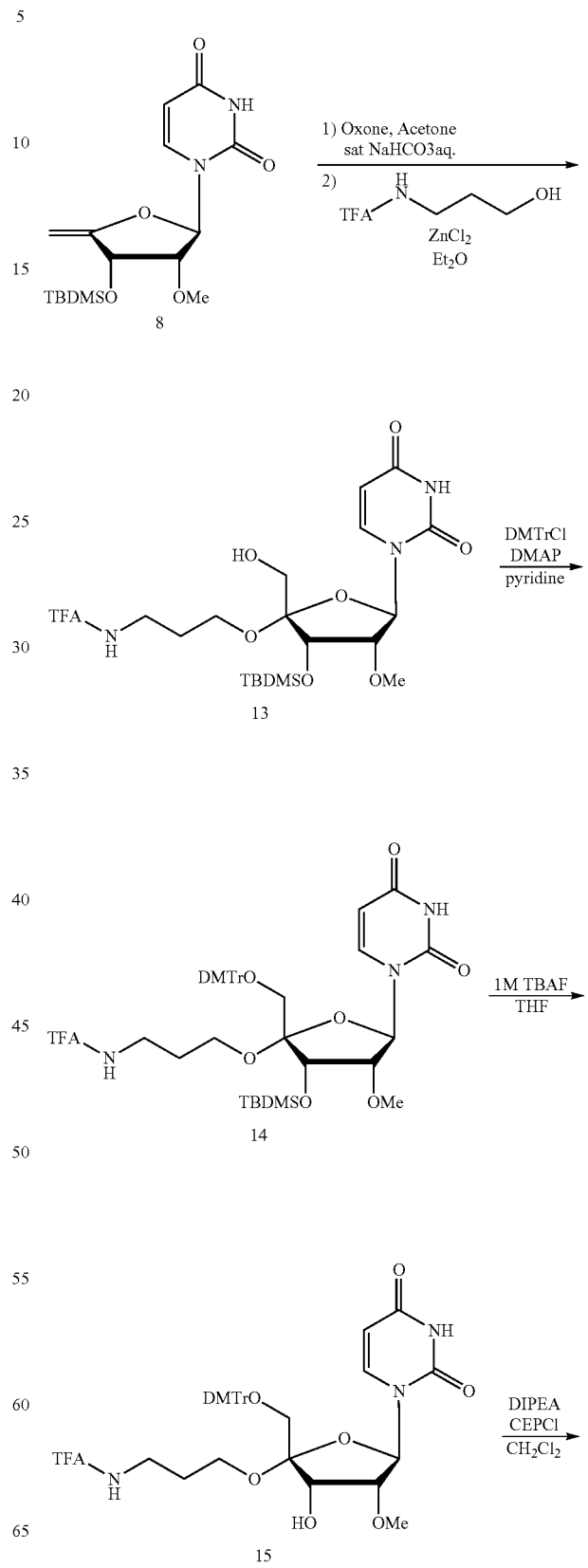

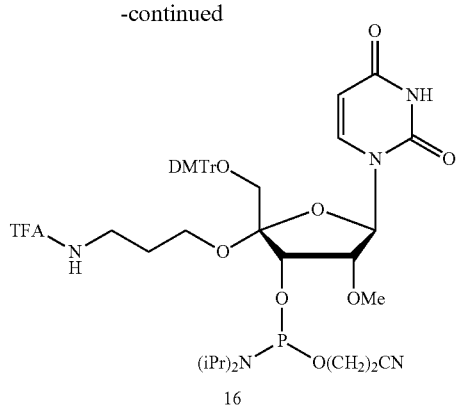

Synthesis of 4'-C-trifluoroacetylaminopropoxyl-3'-O-[(1,1-dimethylethyl)diphenylsilyl]-2'-O-methyl (Compound 13)

In an Ar atmosphere, dichloromethane (7.0 mL) was added to compound 8 (0.35 g, 0.99 mmol) and dissolved, and acetone (7.0 mL) and an aqueous saturated sodium hydrogen carbonate solution (7.0 mL) were added, and an aqueous solution (6.9 mL) of Oxone (0.45 g, 2.97 mmol) was added at 0° C., and stirred at room temperature for 3 hours. The product was then extracted with chloroform and an aqueous saturated sodium hydrogen carbonate solution, the organic phase was washed with an aqueous saturated sodium hydrogen carbonate solution and an aqueous saturated sodium chloride solution, and then dried over sodium sulfate, and the solvent was distilled off under reduced pressure to obtain a crude product. Subsequently, diethyl ether (Et$_2$O, 8 mL) was added to the crude product and dissolved in an Ar atmosphere, and 1.0 M zinc chloride (ZnCl$_2$, 0.16 mmol, 0.16 mL), and [2-(2,2,2-trifluoroacetamide)propoxy]methyl acetate (1.69 g, 1.19 mmol) were added at −40° C., and stirred at room temperature for 12 hours, and then quenched with an aqueous saturated sodium hydrogen carbonate solution, and filtered through Celite. The product was extracted from the filtrate with ethyl acetate and an aqueous saturated sodium hydrogen carbonate solution, the organic phase was washed with water and an aqueous saturated sodium chloride, and then dried over sodium sulfate, and the solvent was distilled off under reduced pressure. The residue was purified by silica gel column chromatography (hexane:ethyl acetate=1:1 (v/v)) to obtain compound 13 (0.22 g, 0.41 mmol, a yield of 42%).

Synthesis of 5'-O-[bis(4-methoxyphenyl)phenylmethyl]-4'-C-trifluoroacetylaminopropoxyl-3'-O-[(1,1-dimethylethyl)diphenylsilyl]-2'-O-methyl-uridine (Compound 14)

In an Ar atmosphere, pyridine (2.5 mL) was added to compound 13 (0.22 g, 0.41 mmol) and dissolved, and 4,4'-dimethoxytriphenylmethyl chloride (DMTrCl, 0.21 g, 0.62 mmol) and N,N-dimethyl-4-aminopyridine (DMAP, 0.05 g, 0.41 mmol) were added at 0° C., and stirred overnight at room temperature. The product was then extracted with chloroform and saturated sodium hydrogen carbonate, the organic phase was washed with saturated sodium hydrogen carbonate and saturated sodium chloride, and then dried over sodium sulfate, and the solvent was distilled off under reduced pressure. The residue was purified by silica gel column chromatography (hexane:ethyl acetate=1:1 (v/v)) to obtain compound 14 (0.24 g, 0.28 mmol, a yield of 68%).

Synthesis of 5'-O-[bis(4-methoxyphenyl)phenylmethyl]-4'-C-trifluoroacetylaminopropoxyl-2'-O-methyl-uridine (Compound 15)

In an Ar atmosphere, THF (0.74 mL) was added to compound 14 (0.11 g, 0.13 mmol) and dissolved, and 1 M tetrabutylammonium fluoride (TBAF, 0.23 mL) was added, and stirred at room temperature for 3 hours. The solvent was then distilled off under reduced pressure. The residue was purified by silica gel column chromatography (hexane:ethyl acetate=1:2 (v/v)) to obtain compound 15 (0.09 g, 0.13 mmol, a yield of 97%).

Synthesis of 5'-O-[bis(4-methoxyphenyl)phenylmethyl]-4'-C-trifluoroacetylaminopropoxyl-2'-O-methyl-3'-[2-cyanoethyl-N,N-bis(1-methylethyl)-phosphoramidite]-uridine (Compound 16)

In an Ar atmosphere, chloroform (2.7 mL) was added to compound 15 (0.27 g, 0.38 mmol) and dissolved, and N,N-diisopropylethylamine (DIPEA, 0.33 mL, 1.86 mmol), and 2-cyanoethyl-N,N-diisopropylchlorophosphoroamidite (CEP-Cl, 0.17 mL, 0.75 mmol) were added, and stirred at room temperature for 1 hour. The product was then extracted with chloroform and an aqueous saturated sodium hydrogen carbonate solution, washed with an aqueous saturated sodium chloride solution, and then dried over sodium sulfate, and the solvent was distilled off under reduced pressure. The residue was purified by silica gel column chromatography (hexane:ethyl acetate=2:3 (v/v)) to obtain compound 16 (0.15 g, 0.17 mmol, a yield of 44%). $^{31}$P NMR (162 MHz, CDCl$_3$) δ: 152.29, 152.72

(3) 2'-OMe-4'-aminopropyl uridine

2'-OMe-4'-aminopropyluridine was synthesized by the method described in WO 2018/11678. More particularly, according to the following scheme, 5'-O-[bis(4-methoxyphenyl)phenylmethyl]-4'-C-trifluoroaminopropyl-2'-O-methyl-3'-[2-cyanoethyl-N,N-bis(1-methylethyl)-phosphoroamidite]-uridine (compound 27) was synthesized.

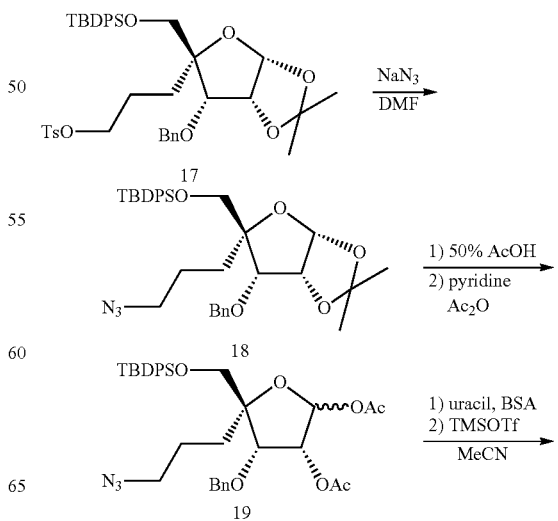

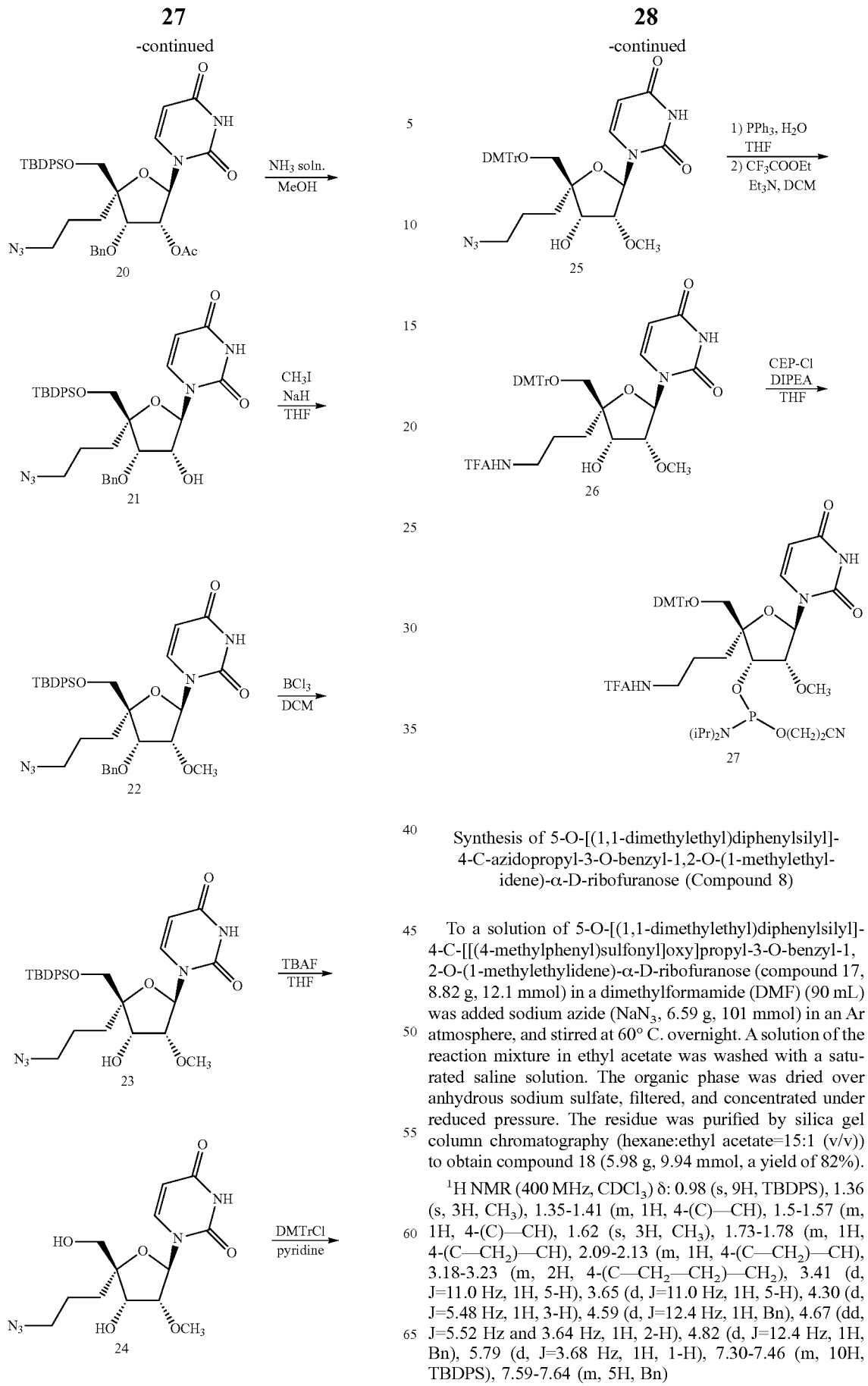

Synthesis of 5-O-[(1,1-dimethylethyl)diphenylsilyl]-4-C-azidopropyl-3-O-benzyl-1,2-O-(1-methylethylidene)-α-D-ribofuranose (Compound 8)

To a solution of 5-O-[(1,1-dimethylethyl)diphenylsilyl]-4-C-[[(4-methylphenyl)sulfonyl]oxy]propyl-3-O-benzyl-1,2-O-(1-methylethylidene)-α-D-ribofuranose (compound 17, 8.82 g, 12.1 mmol) in a dimethylformamide (DMF) (90 mL) was added sodium azide (NaN$_3$, 6.59 g, 101 mmol) in an Ar atmosphere, and stirred at 60° C. overnight. A solution of the reaction mixture in ethyl acetate was washed with a saturated saline solution. The organic phase was dried over anhydrous sodium sulfate, filtered, and concentrated under reduced pressure. The residue was purified by silica gel column chromatography (hexane:ethyl acetate=15:1 (v/v)) to obtain compound 18 (5.98 g, 9.94 mmol, a yield of 82%).

$^1$H NMR (400 MHz, CDCl$_3$) δ: 0.98 (s, 9H, TBDPS), 1.36 (s, 3H, CH$_3$), 1.35-1.41 (m, 1H, 4-(C)—CH), 1.5-1.57 (m, 1H, 4-(C)—CH), 1.62 (s, 3H, CH$_3$), 1.73-1.78 (m, 1H, 4-(C—CH$_2$)—CH), 2.09-2.13 (m, 1H, 4-(C—CH$_2$)—CH), 3.18-3.23 (m, 2H, 4-(C—CH$_2$—CH$_2$)—CH$_2$), 3.41 (d, J=11.0 Hz, 1H, 5-H), 3.65 (d, J=11.0 Hz, 1H, 5-H), 4.30 (d, J=5.48 Hz, 1H, 3-H), 4.59 (d, J=12.4 Hz, 1H, Bn), 4.67 (dd, J=5.52 Hz and 3.64 Hz, 1H, 2-H), 4.82 (d, J=12.4 Hz, 1H, Bn), 5.79 (d, J=3.68 Hz, 1H, 1-H), 7.30-7.46 (m, 10H, TBDPS), 7.59-7.64 (m, 5H, Bn)

Synthesis of 5-O-[(1,1-dimethylethyl)diphenylsilyl]-4-C-azidopropyl-3-O-benzyl-1,2-di-O-acetyl-α-D-ribofuranose (Compound 19)

To compound 18 (0.40 g, 0.665 mmol) was added 50% acetic acid (5.70 mL) and dissolved, and heated under reflux at 120' C. for 1 hour. The reaction mixture was azeotropically dried with ethanol, and pyridine (1.43 mL, 17.7 mmol) and acetic anhydride ($Ac_2O$, 0.95 mL, 10.2 mmol) were added, and stirred overnight in an Ar atmosphere at room temperature. The reaction mixture was cooled in an ice bath, poured into cold water and then extracted with ethyl acetate. The organic phase was washed with an aqueous saturated sodium hydrogen carbonate and a saturated saline solution. The organic phase was dried over anhydrous sodium sulfate, filtered, and concentrated under reduced pressure. The residue was purified by silica gel column chromatography (hexane:ethyl acetate=5:1 (v/v)) to obtain compound 19 (0.314 g, 0.486 mmol, a yield of 74%).

$^1$H NMR (400 MHz, $CDCl_3$) δ: 1.06 (s, 9H, TBDPS), 1.10-1.14 (m, 1H, 4-(C)—CH), 1.54-1.58 (m, 1H, 4-(C)—CH), 1.74-1.77 (m, 1H, 4-(C—$CH_2$)—CH), 1.82 (s, 3H, $CH_3$), 1.84-1.90 (m, 1H, 4-(C—$CH_2$)—CH), 2.10 (s, 3H, $CH_3$), 3.19-3.23 (m, 2H, 4-(C—$CH_2$—$CH_2$)—$CH_2$), 3.59 (dd, J=10.6 Hz and 13.3 Hz, 2H, 5-$H_2$), 4.38 (d, J=5.52 Hz, 1H, 3-H), 4.54 (d, J=11.4 Hz, 1H, Bn), 4.60 (d, J=11.4 Hz, 1H, Bn), 5.36 (d, J=5.48 Hz, 1H, 2-H), 6.13 (s, 1H, 1-H), 7.27-7.64 (m, 15H, Bn and TBDPS)

Synthesis of 5-O-[(1,1-dimethylethyl)diphenylsilyl]-4'-C-azidopropyl-3'-O-benzyl-2'-O-acetyluridine (Compound 20)

To an acetonitrile solution (MeCN, 28 mL) of compound 19 (2.76 g, 4.27 mmol) were added uracil (0.957 g, 8.54 mmol) and N,O-bis(trimethylsilyl)acetamide (BSA, 11.1 mL, 34.2 mmol) in an Ar atmosphere, and heated under reflux at 95° C. for 1 hour. This was cooled to 0° C., and trimethylsilyl trifluoromethanesulfonate (TMSOTf, 1.55 mL, 8.54 mmol) was carefully dropped. After heating and refluxing at 95° C. for 15 minutes again, the mixture was cooled in an ice bath and an aqueous saturated sodium bicarbonate solution was added. The reaction mixture was extracted with chloroform and the organic phase was washed with an aqueous saturated sodium bicarbonate solution. The organic phase was dried over anhydrous sodium sulfate, filtered, and concentrated under reduced pressure. The residue was purified by silica gel column chromatography (hexane:ethyl acetate=2:1 (v/v)) to obtain compound 20 (2.27 g, 3.26 mmol, a yield of 76%).

$^1$H NMR (400 MHz, $CDCl_3$) δ: 1.09 (s, 9H, TBDPS), 1.45-1.51 (m, 2H, 4'-(C)—$CH_2$), 1.64-1.69 (m, 1H, 4'-(C—$CH_2$)—CH), 1.82-1.89 (m, 1H, 4'-(C—$CH_2$)—CH), 2.11 (s, 3H, $CH_2$), 3.18-3.24 (m, 2H, 4'-(C—$CH_2$—$CH_2$)—$CH_2$), 3.56 (d, J=11.4 Hz, 1H, 5'-H), 3.84 (d, J=10.9 Hz, 1H, 5'-H), 4.39-4.44 (m, 2H, 3'-H and Bn), 4.61 (d, J=11.0 Hz, 1H, Bn), 5.32-5.48 (m, 2H, 2'-H and 6-H), 6.18 (d, J=5.04 Hz, 1H, 1'-H), 7.28-7.57 (m, 15H, Bn and TBDPS), 7.67 (d, J=8.24 Hz, 1H, 5-H), 8.66 (s, 1H, 3-NH)

Synthesis of 5-O-[(1,1-dimethylethyl)diphenylsilyl]-4'-C-azidopropyl-3'-O-benzyluridine (Compound 21)

Ammonia water (16 mL) and methanol (MeOH, 16 mL) were added to compound 20 (1.57 g, 2.24 mmol), and stirred overnight at room temperature. Ethanol was added to the reaction mixture, and concentrated under reduced pressure. The residue was purified by silica gel column chromatography (hexane:ethyl acetate=2:1 (v/v)) to obtain compound 21 (1.44 g, 2.19 mmol, a yield of 98%).

$^1$H NMR (400 MHz, $CDCl_3$) δ: 1.09 (s, 9H, TBDPS), 1.37-1.41 (m, 1H, 4'-(C)—CH), 1.51-1.55 (m, 1H, 4'-(C)—CH), 1.61-1.68 (m, 1H, 4'-(C—$CH_2$)—CH), 1.85-1.89 (m, 1H, 4'-(C—$CH_2$)—CH), 3.13-3.19 (m, 2H, 4'-(C—$CH_2$—$CH_2$)—$CH_2$), 3.55 (d, J=11.0 Hz, 1H, 5'-H), 3.60 (d, J=7.80 Hz, 1H, 2'-OH), 3.78 (d, J=11.0 Hz, 1H, 5'-H), 4.19 (d, J=5.96 Hz, 1H, 3'-H), 4.29 (dd, J=5.96 Hz and 12.36 Hz, 1H, 2'-H), 4.59 (d, J=11.4 Hz, 1H, Bn), 4.74 (d, J=11.5 Hz, 1H, Bn), 5.39 (d, J=8.24 Hz, 1H, 6-H), 5.94 (d, J=5.52 Hz, 1H, 1'-H), 7.34-7.60 (m, 15H, Bn and TBDPS), 7.69 (d, J=7.80 Hz, 1H, 5-H), 9.37 (s, 1H, 3-NH)

Synthesis of 5-O-[(1,1-dimethylethyl)diphenylsilyl]-4'-C-azidopropyl-3'-O-benzyl-2'-O-methyl-uridine (Compound 22)

To a solution of compound 21 (5.33 g, 8.10 mmol) in tetrahydrofuran (53 mL) was added 60% sodium hydride (NaH, 0.972 g, 24.3 mmol) in an ice bath in an Ar atmosphere, and stirred at 0° C. for 10 minutes. To the mixture was carefully dropped iodomethane ($CH_3I$, 3.02 mL, 48.6 mmol), and stirred at 0° C. for 8 hours under light-shielding conditions. The reaction mixture was extracted with ethyl acetate and the organic phase was washed with a saturated saline solution. The organic phase was dried over anhydrous sodium sulfate, filtered, and concentrated under reduced pressure. The residue was produced by silica gel column chromatography (hexane:ethyl acetate=3:1 (v/v)) to obtain compound 22 (4.00 g, 5.98 mmol, a yield of 74%).

$^1$H NMR (400 MHz, $CDCl_3$) δ: 1.08 (s, 9H, TBDPS), 1.39-1.46 (m, 1H, 4'-(C)—CH), 1.52-1.60 (m, 1H, 4'-(C)—CH), 1.65-1.70 (m, 1H, 4'-(C—$CH_2$)—CH), 1.97-2.05 (m, 1H, 4'-(C—$CH_2$)—CH), 3.19-3.26 (m, 2H, 4'-(C—$CH_2$—$CH_2$)—$CH_2$), 3.51 (s, 3H, 2'-$OCH_3$), 3.68 (d, J=11.5 Hz, 1H, 5'-H), 3.74 (m, 1H, 2'-H), 3.95 (d, J=11.5 Hz, 1H, 5'-H), 4.35 (d, J=4.60 Hz, 1H, 3'-H), 4.52 (d, J=11.5 Hz, 1H, Bn), 4.73 (d, J=11.9 Hz, 1H, Bn), 5.12 (d, J=8.24 Hz, 1H, 6-H), 6.09 (s, 1H, 1'-H), 7.35-7.63 (m, 15H, Bn and TBDPS), 7.78 (d, J=8.24 Hz, 1H, 5-H), 9.04 (s, 1H, 3-NH)

Synthesis of 5-O-[(1,1-dimethylethyl)diphenylsilyl]-4'-C-azidopropyl-2'-O-methyl-uridine (Compound 23)

In an Ar atmosphere, 60 mL of a dichloromethane (DCM) solution of compound 22 (4.00 g, 5.98 mmol) was cooled to −78° C., and a solution of 1 M boron trichloride ($BCl_3$) in dichloromethane (35.9 mL, 35.9 mmol) was added and stirred for 3 hours. The temperature was then increased to −30° C., and the mixture was stirred for 3 hours. Dichloromethane-methanol (1:1 (v/v), 100 mL) was added to the reaction mixture, and concentrated under reduced pressure. The residue was purified by silica gel column chromatography (hexane:ethyl acetate=1:1 (v/v)) to obtain compound 23 (2.99 g, 5.16 mmol, a yield of 86%).

$^1$H NMR (600 MHz, $CDCl_3$) δ: 1.11 (s, 9H, TBDPS), 1.49-1.56 (m, 2H, 4'-(C)—$CH_2$), 1.58-1.64 (m, 1H, 4'-(C—$CH_2$)—CH), 1.76-1.80 (m, 1H, 4'-(C—$CH_2$)—CH), 2.74 (d, J=5.52 Hz, 1H, 3'-OH), 3.21-3.25 (m, 2H, 4'-(C—$CH_2$—$CH_2$)—$CH_2$), 3.52 (s, 3H, 2'-$OCH_3$), 3.70 (d, J=11.0 Hz, 1H, 5'-H), 3.88 (d, J=11.0 Hz, 1H, 5'-H), 3.93 (m, 1H, 2'-H), 4.49 (t, J=5.46 Hz, 1H, 3'-H), 5.31 (d, J=8.28 Hz, 1H, 6-H), 6.06

(d, J=4.80 Hz, 1H, 1'-H), 7.41-7.66 (m, 10H, TBDPS), 7.08 (d, J=7.56 Hz, 1H, 5-H), 8.04 (s, 1H, 3-NH)

Synthesis of 4'-C-azidopropyl-2'-O-methyl-uridine (Compound 24)

To a solution of compound 23 (2.99 g. 5.16 mmol) in tetrahydrofuran (THF) (30.0 mL) was added a solution of 1 M tetrabutylammonium fluoride in tetrahydrofuran (TBAF) (7.74 mL, 7.74 mmol) in an Ar atmosphere, and stirred overnight at room temperature. The solvent was then concentrated under reduced pressure and the residue was purified by silica gel column chromatography (chloroform:methanol=10:1 (v/v)) to obtain compound 24 (1.68 g, 4.94 mmol, a yield of 96%).

$^1$H NMR (600 MHz, CDCl$_3$) δ: 1.55-1.67 (m, 4H, 4'-(C)—CH$_2$—CH$_2$), 3.27-3.29 (m, 2H, 4'-(C—CH$_2$—CH$_2$)—CH$_2$), 3.32 (s, 3H, 2'-OCH$_3$), 3.42-3.45 (m, 2H, 5'-H$_2$), 3.98 (dd, J=7.56 Hz and 4.80 Hz, 1H, 2'-H), 4.16 (t, J=5.46 Hz, 1H, 3'-H), 5.13 (d, J=6.18 Hz, 1H, 3'-OH), 5.20 (d, J=5.46 Hz, 1H, 5'-OH), 5.67 (d, J=8.28 Hz, 1H, 6-H), 5.90 (d, J=6.84 Hz, 1H, 1'-H), 7.89 (d, J=8.22 Hz, 1H, 5-H), 11.34 (s, 1H, 3-NH)

Synthesis of 5'-O-[bis(4-methoxyphenyl)phenylmethyl]-4'-C-azidopropyl-2'-O-methyl-uridine (Compound 25)

To a solution (17 mL) of compound 24 (1.68 g, 4.94 mmol) in pyridine was added 4,4'-dimethoxytrityl chloride (DMTrCl, 2.51 g, 7.41 mmol) in an Ar atmosphere, and stirred at room temperature for 5 hours. The reaction mixture was extracted with ethyl acetate, and the organic phase was washed with an aqueous saturated sodium bicarbonate and a saturated saline solution. The organic phase was dried over anhydrous sodium sulfate, filtered, and concentrated under reduced pressure. The residue was purified by silica gel column chromatography (hexane:ethyl acetate=1:1 (v/v)) to obtain compound 25 (3.12 g, 4.85 mmol, a yield of 98%).

$^1$H NMR (400 MHz, CDCl$_3$) δ: 1.38-1.44 (m, 1H, 4'-(C)—CH), 1.54-1.64 (m, 2H, 4'-(C)—CH—CH), 1.78-1.84 (m, 1H, 4'-(C—CH$_2$)—CH), 2.77 (d. J=6.44 Hz, 1H, 3'-OH), 3.17-3.22 (m, 2H, 4'-(C—CH$_2$—CH$_2$)—CH$_2$), 3.34 (s, 2H, 5'-H$_2$), 3.57 (s, 3H, 2'-OCH$_3$), 3.80 (s, 6H, DMTr), 3.92 (dd, J=4.12 Hz and 5.96 Hz, 1H, 2'-H), 4.60 (t, J=5.96 Hz, 1H, 3'-H), 5.22 (d, J=8.24 Hz, 1H, 6-H), 6.02 (d, J=4.12 Hz, 1H, 1'-H), 6.84-7.36 (m, 13H, DMTr), 7.82 (d, J=8.24 Hz, 1H, 5-H), 8.09 (s, 1H, 3-NH)

Synthesis of 5'-O-[bis(4-methoxyphenyl)phenylmethyl]-4'-C-trifluoroacetylaminopropyl-2'-O-methyl-uridine (Compound 26)

Triphenylphosphine (PPh$_3$, 3.12 g, 4.85 mmol) and water (3.50 mL, 194 mmol) were added to a solution of compound 25 (3.12 g, 4.85 mmol) in tetrahydrofuran (THF) (62.4 mL), and stirred at 45° C. for 20 hours. Tetrahydrofuran in the reaction mixture was distilled off under reduced pressure, and a solution (30 mL) of dichloromethane (DCM) was formed. Ethyl trifluoroacetate (CF$_3$COOEt, 1.74 mL, 14.5 mmol) and triethylamine (Et$_3$N, 1.00 mL, 7.28 mmol) were added, and stirred at room temperature for 24 hours. The reaction mixture was extracted with ethyl acetate and the organic phase was washed with a saturated saline solution. The organic phase was dried over anhydrous sodium sulfate, filtered, and concentrated under reduced pressure. The residue was purified by silica gel column chromatography (hexane:ethyl acetate=1:1 (v/v)) to quantitatively obtain compound 26.

$^1$H NMR (400 MHz, CDCl$_3$) δ: 1.40-1.45 (m, 1H, 4'-(C)—CH), 1.63-1.67 (m, 1H, 4'-(C—CH$_2$)—CH), 1.72-1.78 (m, 1H, 4'-(C—CH$_2$)—CH), 2.88 (d, J=4.56 Hz, 1H, 3'-OH), 3.25-3.28 (m, 2H, 4'-(C—CH$_2$—CH$_2$)—CH$_2$), 3.30 (d, J=10.5 Hz, 1H, 5'-H), 3.35 (d, J=10.1 Hz, 1H, 5'-H), 3.54 (s, 3H, 2'-OCH$_3$), 3.80 (s, 6H, DMTr), 4.03 (t, J=5.04 Hz, 1H, 2'-H), 4.54 (t, J=5.04 Hz, 1H, 3'-H), 5.26 (d, J=8.24 Hz, 1H, 6-H), 6.03 (d, J=5.04 Hz, 1H, 1'-H), 6.66 (m, 1H, —NHCOCF$_3$), 6.84-7.55 (m, 13H, DMTr), 7.74 (d, J=8.24 Hz, 1H, 5-H), 8.17 (s, 1H, 3-NH)

Synthesis of 5'-O-[bis(4-methoxyphenyl)phenylmethyl]-4'-C-trifluoroaminopropyl-2'-O-methyl-3'-[2-cyanoethyl-N,N-bis(1-methylethyl)-phosphoramidite]-uridine (Compound 27)

To a solution of compound 26 (1.55 g, 2.17 mmol) in tetrahydrofuran (THF) (15 mL) were added N,N-diisopropylethylamine (DIPEA, 1.90 mL, 10.9 mmol), and 2-cyanoethyl-N,N-diisopropylchlorophosphoramidite (CEP-Cl, 0.97 mL, 4.34 mmol) in an Ar atmosphere, and stirred at room temperature for 1 hour. The reaction mixture was extracted with ethyl acetate, and the organic phase was washed with an aqueous saturated sodium bicarbonate and a saturated saline solution. The organic phase was dried over anhydrous sodium sulfate, filtered, and concentrated under reduced pressure. The residue was purified by silica gel column chromatography (hexane:ethyl acetate=1:1 (v/v)) to obtain compound 27 (1.57 g, 1.71 mmol, a yield of 79%).

$^{31}$P NMR (243 MHz. CDCl$_3$) δ: 150.57, 151.44

(4) 4'-aminoethoxythymidine

According to the following scheme, using compound 28 as a starting material, 4'-C-α-trifluoroacetylaminoethoxy-3'-O-[2-cyanoethoxy(diisopropylamino)phosphino]-5'-O-[bis(4-methoxyphenyl)phenylmethyl]-3'-O-tert-butyldimethylsilyl-thymidine (compound 32) was synthesized.

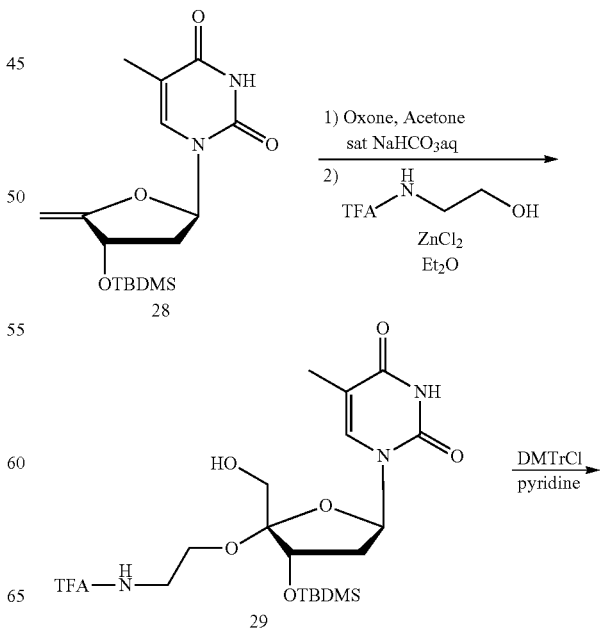

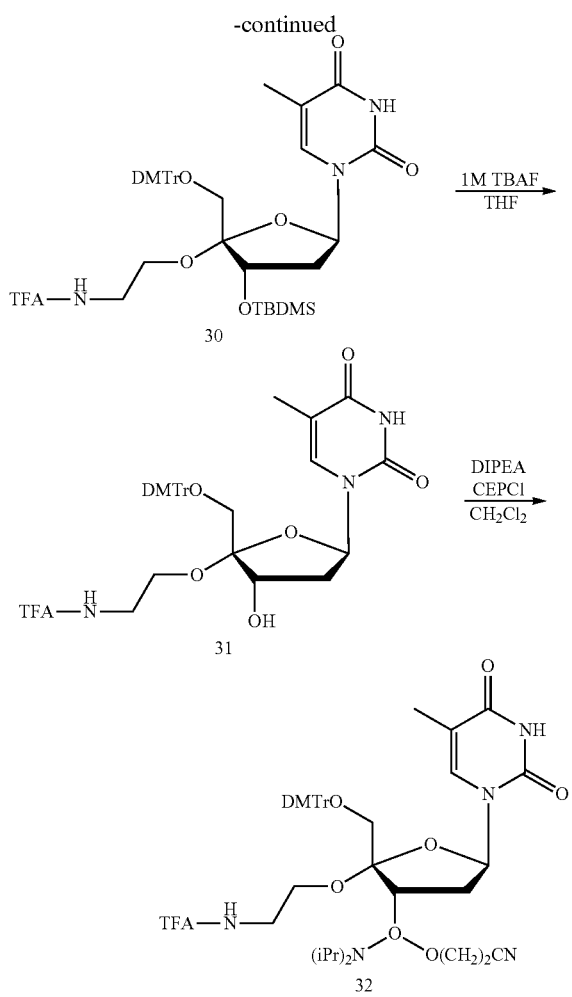

Synthesis of 4'-C-α-trifluoroacetylaminoetho-3'-O-tert-butyldimethylsilyl-thymidine (compound 29)

Compound 28 (1.54 g, 4.56 mmol) was dissolved in dichloromethane (32 mL), and acetone (32 mL) and an aqueous saturated sodium hydrogen carbonate solution (32 mL) were added in an ice bath, and a solution of potassium peroxymonosulfate (Ozone®, 2.0842 g, 13.68 mmol) dissolved in distilled water (32 mL) was then dropped. After stirring in an ice bath for 0.5 hours, the product was extracted from the reaction solution using chloroform and an aqueous saturated sodium hydrogen carbonate solution, the organic phase was washed with an aqueous saturated sodium chloride solution, and water was then removed with sodium sulfate. Subsequently, the solvent was removed under reduced pressure to obtain a crude product.

Subsequently, in an Ar atmosphere, the crude product was dissolved in tetrahydrofuran (THF, 7 mL), and zinc chloride (0.6283 g, 4.56 mmol) was added at −40° C., and a solution of aminoethanol TFA (3.5872 g, 22.8 mmol) dissolved in THF (2 mL) was then dropped therein. The term "aminoethanol TFA" means aminoethanol in which an amino group is protected by a trifluoroacetyl group. Subsequently, the mixture was returned to room temperature, stirred, and, after 20.5 hours, quenched with an aqueous saturated sodium hydrogen carbonate solution. The precipitated salt was removed by filtration through Celite, the resulting compound was extracted from the filtrate using ethyl acetate and an aqueous saturated hydrogen carbonate solution, and the organic phase was washed with an aqueous saturated sodium chloride solution, and water was then removed with sodium sulfate, and the solvent was distilled off under reduce pressure. The residue was purified by silica gel column chromatography (hexane/ethyl acetate=1:1 (v/v)) to obtain compound 29 (0.9302 g, a yield of 39%), $^1$H-NMR (400 MHz, CDCl$_3$) δ: 8.30 (s, 1H), 7.22 (d, J=0.9 Hz, 1H), 6.97 (d, J=22.4 Hz, 1H), 6.14 (dd, J=7.3, 5.0 Hz, 1H), 4.67 (t, J=7.3 Hz, 1H), 3.94-3.89 (m, 1H), 3.82-3.76 (m, 2H), 3.70 (dd, J=11.4, 6.9 Hz, 1H), 3.62-3.56 (m, 1H), 3.53-3.46 (m, 1H), 2.49-2.36 (m, 2H), 2.32 (dd, J=6.9, 4.6 Hz, 1H), 1.93 (d, J=0.9 Hz, 3H), 0.90 (s, 9H), 0.11 (s, 3H), −0.002 (s, 3H)

Synthesis of 4'-C-α-trifluoroacetylaminoethoxy-5-O-[bis(4-methoxyphenyl)phenylmethyl]-3'-O-tert-butyldimethylsilyl-thymidine (Compound 30)

In an Ar atmosphere, compound 29 (1.1481 g, 2.24 mmol) was dissolved in pyridine (11.5 mL), and 4,4'-dimethoxytriphenylmethyl chloride (DMTrCl, 0.8749 g, 2.58 mmol) was added, and stirred at room temperature for 24 hours. The solvent was then removed under reduced pressure, and the residue was purified by silica gel column chromatography (hexane/ethyl acetate=1:1 (v/v)) to obtain compound 30 (1.7707 g, a yield of 97%), $^1$H-NMR (400 MHz, CDCl$_3$) δ: 8.08 (s, 1H), 7.34-7.20 (m, 10H), 6.83 (dd, J=9.3, 2.5 Hz, 4H), 6.69 (brs, 1H), 6.33 (dd, J=7.3, 4.6 Hz, 1H), 4.76 (t, J=7.3 Hz, 1H), 3.80 (s, 6H), 3.64-3.47 (m, 4H), 3.46-3.32 (m, 1H), 3.17 (d, J=9.6 Hz, 1H), 2.52-2.40 (m, 1H), 2.39-2.25 (m, 1H), 1.37 (d, J=0.9 Hz, 3H), 0.81 (s, 9H), 0.02 (s, 3H), −0.05 (s, 3H)

Synthesis of 4'-C-α-trifluoroacetylaminoethoxy-5'-O-[bis(4-methoxyphenyl)phenylmethyl]-thymidine (Compound 31)

In an Ar atmosphere, compound 30 (1.77 g, 2.17 mmol) was dissolved in THF (22 mL), and 1M tetrabutylammonium fluoride (TBAF, 3.26 mL) was added, and stirred at room temperature for 0.5 hours. The solvent was then removed under reduced pressure, and the residue was purified by silica gel column chromatography (hexane/ethyl acetate=1:2 (v/v)) to obtain compound 31 (1.3391 g, a yield of 88%).

$^1$H-NMR (400 MHz, CDCl$_3$) δ: 7.31-7.21 (m, 11H), 6.84 (dd, J=8.9, 1.1 Hz, 4H), 6.31 (dd, J=6.9, 5.0 Hz, 1H), 4.68 (t, J=7.3 Hz, 1H), 3.86-3.68 (m, 6H), 3.76-3.73 (m, 1H), 3.62-3.40 (m, 4H), 3.32 (d, J=10.1 Hz, 1H), 2.50-2.32 (m, 2H), 1.49 (d, J=0.9 Hz, 3H)

Synthesis of 4'-C-α-trifluoroacetylaminoethoxy-3'-O-[2-cyanoethoxy(diisopropylamino)phosphino]-5'-O-[bis(4-methoxyphenyl)phenylmethyl]-3'-O-tert-butyldimethylsilyl-thymidine (Compound 32)

In an Ar atmosphere, compound 31 (0.751 g, 1.07 mmol) was dissolved in dichloromethane (7.5 mL), and N,N-diisopropylethylamine (1.00 mL, 5.37 mmol) and 2-cyanoethyl-N,N-diisopropylchlorophosphoroamidite (CEP-Cl, 0.50 mL, 2.15 mmol) were added, and stirred at room temperature for 0.5 hours. The product was then extracted from the reaction solution using chloroform and an aqueous saturated sodium hydrogen carbonate solution, the organic phase was washed with an aqueous saturated sodium chloride solution, and water was then removed with sodium sulfate. The solvent was then removed under reduced pressure, and the residue was purified by silica gel column chromatography (hexane/ethyl acetate=2:3 (v/v)) to obtain compound 32 (0.678 g, 0.753 mmol, a yield of 75%).

$^{31}$P-NMR (162 MHz, CDCl$_3$) δ: 150.6, 149.6

Synthesis of Solid-Phase Support (1) 2'-OMe-4'-aminoethoxyuridine-supported CPG Support In an Ar atmosphere, to a solution of 5-O-[bis(4-methoxyphenyl)phenylmethyl]-4'-C-trifluoroacetylaminoethoxyl-2'-O-methyl-uridine (compound 11) in pyridine were added N-dimethyl-4-aminopyridine (DMAP) and succinic anhydride, and stirred at room temperature. The reaction mixture was extracted with ethyl acetate and the organic phase was washed with an aqueous saturated sodium bicarbonate. The organic phase was dried over anhydrous sodium sulfate, filtered, and concentrated under reduced pressure. Dimethylformamide was added to the residue and dissolved, and controlled pore glass (CPG) and 1-(3-dimethylaminopropyl)-3-ethylcarbodiimide hydrochloride (EDC) were added and shaken. CPG was separated through a filter, and washed with pyridine. Subsequently, DMAP, pyridine and acetic anhydride were added in an Ar atmosphere, and the mixture was allowed to stand. CPG was filtered, washed with pyridine, ethanol and acetonitrile and then dried to obtain a 5'-O-[bis(4-methoxyphenyl)phenylmethyl]-4'-C-trifluoroacetylaminoethoxyl-2'-O-methyl-uridine-supported CPG support.

(2) 2'-OMe-4'-aminopropoxyuridine-Supported CPG Ssupport

In an Ar atmosphere, to a solution of 5'-O-[bis(4-methoxyphenyl)phenylmethyl]-4'-C-trifluoroacetylaminopropoxyl-2'-O-methyl-uridine (compound 15) in pyridine were added N,N-dimethyl-4-aminopyridine (DMAP) and succinic anhydride and stirred at room temperature. The reaction mixture was extracted with ethyl acetate and the organic phase was washed with an aqueous saturated sodium bicarbonate. The organic phase was dried over anhydrous sodium sulfate, filtered, and concentrated under reduced pressure. Dimethylformamide was added to the residue and dissolved, and controlled pore glass (CPG) and 1-(3-dimethylaminopropyl)-3-ethylcarbodiimide hydrochloride (EDC) were added and shaken. CPG was separated through a filter, and washed with pyridine. Subsequently, DMAP, pyridine and acetic anhydride were added in an Ar atmosphere, and the mixture was allowed to stand. CPG was filtered, washed with pyridine, ethanol and acetonitrile, and dried to obtain a 5'-O-[bis(4-methoxyphenyl)phenylmethyl]-4'-C-trifluoroacetylaminopropoxyl-2'-O-methyl-uridine-supported CPG support.

(3) 2'-OMe-4'-aminopropyl uridine-Supported CPG Ssupport

In an Ar atmosphere, to a solution of 5'-O-[bis(4-methoxyphenyl)phenylmethyl]-4'-C-trifluoroacetylaminopropyl-2'-O-methyl-uridine (compound 26: 0.142 g, 0.20 mmol) in pyridine (1.4 mL) were added N,N-dimethyl-4-aminopyridine (DMAP, 48.9 mg, 0.40 mmol) and succinic anhydride (80.1 mg, 0.80 mmol), and stirred at room temperature for 24 hours. The reaction mixture was extracted with ethyl acetate and the organic phase was washed with an aqueous saturated sodium bicarbonate. The organic phase was dried over anhydrous sodium sulfate, filtered, and concentrated under reduced pressure. Dimethylformamide (2.0 mL) was added to the residue and dissolved, and controlled pore glass (CPG, 0.373 g) and 1-(3-dimethylaminopropyl)-3-ethylcarbodiimide hydrochloride (EDC, 38.3 mg, 0.20 mmol) were added and shaken for 4 days. CPG was separated through a filter, and washed with pyridine. Subsequently, DMAP (0.183 g), pyridine (13.5 mL) and acetic anhydride (1.5 mL) were added in an Ar atmosphere, and the mixture was allowed to stand for 16 hours. CPG was filtered, washed with pyridine, ethanol and acetonitrile and then dried to obtain a 5'-O-[bis(4-methoxyphenyl)phenylmethyl]-4'-C-trifluoroacetylaminopropyl-2'-O-methyl-uridine-supported CPG support (an activity of 35.8 µmol/g).

(4) 4'-aminoethoxythymidine-Supported CPG Support

In an Ar atmosphere, to a solution of 4'-C-α-trifluoroacetylaminoethoxy-5'-O-[bis(4-methoxyphenyl)phenylmethyl]-thymidine (compound 31) in pyridine were added N,N-dimethyl-4-aminopyridine (DMAP) and succinic anhydride, and stirred at room temperature. The reaction mixture was extracted with ethyl acetate and the organic phase was washed with an aqueous saturated sodium bicarbonate. The organic phase was dried over anhydrous sodium sulfate, filtered, and concentrated under reduced pressure. Dimethylformamide was added to the residue and dissolved, and controlled pore glass (CPG) and 1-(3-dimethylaminopropyl)-3-ethylcarbodiimide hydrochloride (EDC) were added and shaken. CPG was separated through a filter, and washed with pyridine. Subsequently, DMAP, pyridine and acetic anhydride were added in an Ar atmosphere, and the mixture was allowed to stand. CPG was filtered, washed with pyridine, ethanol and acetonitrile and dried to obtain a 4'-C-α-trifluoroacetylaminoethoxy-5'-O-[bis(4-methoxyphenyl)phenylmethyl]-thymidine-supported CPG support.

Synthesis of Oligonucleotide Derivatives (1) Synthesis of oligonucleotide Derivatives (11 mer and 21 mer)

Oligonucleotide derivatives (11 mer and 21 mer were synthesized by an automated nucleic acid synthesizer with the phosphoramidite method using the (1) to (3) nucleoside derivatives (amidites) synthesized above and the solid-phase supports. In this case, each amidite was diluted with acetonitrile so as to have 0.1 to 0.15 M. At the end of the synthesis, the product (CPG resin) was transferred to a sampling tube, and a mixture of acetonitrile and diethylamine (9:1 (v/v), 1.0 mL) was added and stirred for 5 minutes. The supernatant was then removed and washed twice with acetonitrile (1.0 mL). A mixture of ammonia water and methylamine (1:1 (v/v), 1.0 mL) was then added, and allowed to stand at 65° C. for 10 minutes. A temperature of the solution was then returned to room temperature, and the supernatant was then transferred to a 1.5 mL tube, and a mixture of ethanol and water (3:1 (v/v), 1.0 mL) was added, washed twice, and then dried under reduced pressure. Subsequently, it was dissolved in DMSO (100 µL), and triethylamine (TEA).3HF (125 mL) were added and stirred, and then allowed to stand at 65° C. for 90 minutes. The solution was then brought to 10 mL by 0.1 M triethylamine-acetate buffer (TEAA) and adsorbed through an equilibrated Sep-Pac tC18 reverse phase column.

The column was washed with sterile water, eluted with a mixture of acetonitrile and water (1:1 (v/v), 3 mL), and dried under reduced pressure to obtain a crude product. The crude product was dissolved in a loading solution (1×TBE in 90% formamide) (200 μL) and purified by 20% PAGE (500 V, 20 mA). Subsequently, 0.1 M triethylamine-acetate buffer and an aqueous 1 mM ethylenediaminetetraacetic acid (EDTA) solution (10 mL) were added, and shaken overnight. After shaking, the filtrate was passed through an equilibrated Sep-Pac tC18 reverse phase column and adsorbed on the column. The column was washed with sterile water to remove salts, eluted with acetonitrile-water (1:1 (v/v), 3 mL) and dried under reduced pressure.

For each of the oligonucleotide derivatives obtained as described above, a sample corresponding to 60 μmol was mixed with 3 μL of sterile water and 3 μL of matrix solution, dried on a plate, and then measured for the molecular weight by MALDI-TOF/MS to confirm that it had the predetermined sequence.

(2) Synthesis of Oligonucleotide Derivative (16 mer)

An oligonucleotide derivative (16 mer) was synthesized by an automated nucleic acid synthesizer with the phosphoramidite method using the (4) nucleoside derivative (amidite) synthesized above and the solid-phase support. In this case, the amidite was diluted with acetonitrile so as to have 0.1 to 0.15 M. At the end of the synthesis, the product (CPG resin) was transferred to a sampling tube, and a mixture of acetonitrile and diethylamine (9:1 (v/v), 1.0 mL) was added and stirred for 5 minutes. The supernatant was then removed and washed twice with acetonitrile (1.0 mL). Subsequently, for the synthesis of a DNA oligonucleotide, 28% ammonia water (1 mL) was added and allowed to stand at 55° C. for 12 hours, and for the synthesis of an RNA oligonucleotide, 28% ammonia water (500 μL) and 40% methylamine water and 40% methylamine water (500 μL) were added and allowed to stand at 65° C. for 10 min. A temperature of the solution was then returned to room temperature, and the supernatant was then transferred to a 1.5 mL tube. Subsequently, for the synthesis of the DNA oligonucleotide, water (1.0 mL) was added, and for the synthesis of the RNA oligonucleotide, ethanol and water (1:3 (v/v), 1.0 mL) were added, and washed twice, and dried under reduced pressure. Subsequently, the dried product was dissolved in DMSO (100 μL), and triethylamine (TEA).3HF (125 mL) were added and stirred, and then allowed to stand at 65° C. for 90 minutes. The solution was then brought to 10 mL by 0.1 M triethylamine-acetate buffer (TEAA) and adsorbed through an equilibrated Sep-Pac tC18 reverse phase column. The column was washed with sterile water, and then eluted with a mixture of acetonitrile and water (1:1 (v/v), 3 mL), and dried under reduced pressure to obtain a crude product. The crude product was dissolved in a loading solution (1×TBE in 90% formamide) (200 μL) and purified by 20% PAGE (500 V, 20 mA). Subsequently, 0.1 M triethylamine-acetate buffer and an aqueous 1 mM ethylenediaminetetraacetic acid (EDTA) solution (10 mL) were added, and shaken overnight. After shaking, the filtrate was passed through an equilibrated Sep-Pac tC18 reverse phase column and adsorbed on the column. The column was washed with sterile water to remove salts, eluted with acetonitrile-water (1:1 (v/v), 3 mL) and dried under reduced pressure.

For the oligonucleotide derivative obtained as described above, a sample corresponding to 60 μmol was mixed with 3 μL of sterile water and 3 μL of matrix solution, dried on a plate, and then measured for the molecular weight by MALDI-TOF/MS to confirm that it had the predetermined sequence.

The details of "0.1M triethylamine-acetate buffer (TEAA)", "20% PAGE", "aqueous 1 mM ethylenediaminetetraacetic acid (EDTA) solution" and "matrix solution" used in the synthesis of the oligonucleotide derivatives are as follows:

The "0.1M triethylamine-acetic acid buffer (TEAA)" was used by diluting 2N triethylamine-acetic acid buffer (prepared by adding 277.6 mL of triethylamine to 114.38 mL of acetic acid, adjusting the amount to 1000 mL with water and adjusting the pH to 7.0) by 20 times.

The "20% PAGE" was prepared as follows: 40% acrylamide solution (40 mL), urea (33.6 g) and 10×TBE buffer (8 mL) were added and dissolved, and water was added to 80 mL. To this solution was added ammonium persulfate (55 mg) and dissolved, and TEMED (N,N,N',N'-tetramethylethylenediamine, 40 μL) was added and shaken, and poured between two glass sheets fixed via a 1.5 mm spacer, and allowed to stand for 1 hour or more to solidify. Further, 1×TBE buffer was used as a buffer solution for electrophoresis. The 40% acrylamide solution was prepared by dissolving acrylamide (190 g) and N,N'-bisacrylamide (10 g) in water to adjust the amount to 500 mL. Also, the TBE buffer was prepared by dissolving tris(hydroxymethyl)aminomethane (109 g), boric acid (55 g), and EDTA.2Na (7.43 g) in water and adjusted to have 1000 mL.

The "aqueous 1 mM ethylenediaminetetraacetic acid (EDTA) solution" was used by diluting an aqueous 0.1 M EDTA solution (prepared by dissolving EDTA.4Na (1.80 g) in 40 mL of water) by 100 times.

The "matrix solution" was prepared by dissolving 3-hydroxypicolinic acid (3-HPA, 4.85 mg) and diammonium hydrogen citrate (0.8 mg) in an aqueous 50% acetonitrile solution (50 μL). In addition, diammonium hydrogen citrate was added to inhibit the adhesion of $Na^+$ and $K^+$.

Synthesis of Double-Stranded RNA (11 mer)

The double-stranded RNA was synthesized by adding an equimolar of each strand (oligonucleotide derivative) to PBS buffer, heating it at 90° C. for 5 minutes, and then slowly cooling it to room temperature.

(1) Duplex 1

Sense Strand (5' to 3' direction)
(SEQ ID NO: 1)
UUCUUCUUCUU

Antisense Strand (5' to 3' direction)
(SEQ ID NO: 2)
AAGAAGAAGAA (2) Duplex 2

Sense Strand (5' to 3' direction)
(SEQ ID NO: 1)
UUCUUCU$^{4P}$UCUU

Antisense Strand (5' to 3' direction)
(SEQ ID NO: 2)
AAGAAGAAGAA

Here, $U^{Ap}$ represents a partial structure having an aminopropyl group at the 4' position of ribose (a partial structure derived from 2'-OMe-4'-aminopropyl uridine).

(3) Duplex 3

```
Sense Strand (5' to 3' direction)
                                              (SEQ ID NO: 1)
UUCUUCU^AetxUUCUU Antisense Strand (5' to 3' direction)
                                              (SEQ ID NO: 2)
AAGAAGAAGAA
```

Here, $U^{Aetx}$ represents a partial structure having an aminoethoxy group at the 4' position of ribose (a partial structure derived from 2'-OMe-4'-aminoethoxyuridine).

Evaluation of Thermal Stability

A sample prepared by adding 200 μL of phosphate buffer for Tm to 600 pmol of the double-stranded RNA obtained above was heated at 100° C. for 3 minutes, and then allowed to stand for 1 hour or more to return the temperature to room temperature. 160 μL of the sample was transferred to a dedicated cell, and the absorbance at 260 nm in association with dissociation to a single strand was measured while changing the temperature from 5° C. to 80° C. (0.5° C./min). A 50% melting temperature (Tm) was calculated from a sigmoid curve obtained by plotting the temperatures on the horizontal axis and the absorbances on the vertical axis. The results are shown in Table 1. Table 1 also shows a difference (ΔTm) in Tm of each Duplex with respect to Tm of Duplex 1, which is an evaluation criterion. The drawing results of the melting curves are shown in FIG. 1.

TABLE 1

| No. | Sense Strand (5'→3')<br>Antisense Strand (3'→5) | Tm<br>(° C.) | ΔTm<br>(° C.) |
|---|---|---|---|
| Duplex 1 | UUCUUCUUCUU<br>AAGAAGAAGAA | 42.8 | — |
| Duplex 2 | UUCUUCUPUCUU<br>AAGAAGAAGAA | 39.4 | -3.4 |
| Duplex 3 | UUCUUCUAUCUU<br>AAGAAGAAGAA | 42.2 | -0.6 |

As shown in Table 1, when compared with Duplex 1 (positive control), Duplex 2 with $U^{Ap}$ introduced decreased the Trot by 3.4° C., whereas Duplex 3 with $U^{Aetx}$ introduced decreased the Tm by only 0.6° C., which confirmed that the thermal stability was equivalent to that of Duplex 1.

Synthesis of Double-Stranded RNA/DNA (16 mer)

The double-stranded RNA/DNA was synthesized by adding an equimolar of each strand (oligonucleotide derivative) to PBS buffer, heating it at 90° C. for 5 minutes, and then slowly cooling it to room temperature.

(1) Duplex 4

```
Sense Strand (5' to 3' direction)
                                              (SEQ ID NO: 3)
TCTTTCTCTTTCCCTT Antisense Strand (5' to 3' direction)
                                              (SEQ ID NO: 4)
AAGGGAAAGAGAAAGA
```

(2) Duplex 5

```
Sense Strand (5' to 3' direction)
                                              (SEQ ID NO: 3)
TCTTTCT^AetxCTTTCCCTT Antisense Strand (5' to 3' direction)
                                              (SEQ ID NO: 4)
AAGGGAAAGAGAAAGA
```

Here, $T^{Aetx}$ represents a partial structure having an aminoethoxy group at the 4' position of ribose (a partial structure derived from 4'-aminoethoxythymidine).

Evaluation of Thermal Stability

A sample prepared by adding 200 μL of phosphate buffer for Tm to 600 pmol of the double-stranded RNA/DNA obtained above was heated at 100 for 3 minutes, and then allowed to stand for 1 hour or more to return the temperature to room temperature. 160 μL of the sample was transferred to a dedicated cell, and the absorbance at 260 nm in association with dissociation to a single strand was measured while changing the temperature from 5° C. to 80° C. (0.5° C./min). A 50% melting temperature (Tm) was calculated from a sigmoid curve obtained by plotting the temperatures on the horizontal axis and the absorbances on the vertical axis. The results are shown in Table 2. Table 2 also shows a difference (ΔTm) in Tm of each Duplex with respect to Tm of Duplex 4, which is an evaluation criterion.

TABLE 2

| No. | Sense Strand (5'→3')<br>Antisense Strand (3'→5') | Tm<br>(° C.) | ΔTm<br>(° C.) |
|---|---|---|---|
| Duplex 4 | TCTTTCTCTTTCCCTT<br>AGAAAGAGAAAGGGAA | 59.1 | — |
| Duplex 5 | TCTTTCT^AetxCTTTCCCTT<br>AGAAAGAGAAAGGGAA | 58.3 | -0.8 |

As shown in Table 2, when compared with Duplex 4 (positive control), Duplex 5 with $U^{Aetx}$ introduced decreased the Tm by only 0.8° C., which confirmed that the thermal stability was equivalent to that of Duplex 4.

Synthesis of siRNA (21 mer)

The siRNA was synthesized by adding an equimolar of each strand (oligonucleotide derivative) to PBS buffer, heating it at 90° C. for 5 minutes, and then slowly cooling it to room temperature.

(1) siRNA 1

```
Sense Strand (5' to 3' direction)
                                  (SEQ ID NO: 5)
GGCCUUUCACUACUAAUACUU Antisense Strand (5' to 3' direction)
                                  (SEQ ID NO: 6)
GUAGGAGUAGUGAAAGGCCTT
```

(2) siRNA 2

```
Sense Strand (5' to 3' direction)
                                  (SEQ ID NO: 5)
GGCCUUUCACUACUAAU^{Ap}ACUU Antisense Strand (5' to 3' direction)
                                  (SEQ ID NO: 6)
GUAGGAGUAGUGAAAGGCCTT
```

(3) siRNA 3

```
Sense Strand (5' to 3' direction)
                                  (SEQ ID NO: 5)
GGCCUUUCACU^{Ap}ACUAAUACUU Antisense Strand (5' to 3' direction)
                                  (SEQ ID NO: 6)
GUAGGAGUAGUGAAAGGCCTT
```

(4) siRNA 4

```
Sense Strand (5' to 3' direction)
                                  (SEQ ID NO: 5)
GGCCUUU^{Ap}CACUACUAAUACUU Antisense Strand (5' to 3' direction)
                                  (SEQ ID NO: 6)
GUAGGAGUAGUGAAAGGCCTT
```

(5) siRNA 5

```
Sense Strand (5' to 3' direction)
                                  (SEQ ID NO: 5)
GGCCUUUCACUACUAAU^{Aetx}ACUU Antisense Strand (5' to 3' direction)
                                  (SEQ ID NO: 6)
GUAGGAGUAGUGAAAGGCCTT
```

(6) siRNA 6

```
Sense Strand (5' to 3' direction)
                                  (SEQ ID NO: 5)
GGCCUUUCACU^{Aetx}ACUAAUACUU Antisense Strand (5' to 3' direction)
                                  (SEQ ID NO: 6)
GUAGGAGUAGUGAAAGGCCTT
```

(7) siRNA 7

```
Sense Strand (5' to 3' direction)
                                  (SEQ ID NO: 5)
GGCCUUU^{Aetx}CACUACUAAUACUU Antisense Strand (5' to 3' direction)
                                  (SEQ ID NO: 6)
GUAGGAGUAGUGAAAGGCCTT
```

Evaluation of Thermal Stability

A sample prepared by adding 200 μL of phosphate buffer for Tm to 600 pmol of the siRNA obtained above was heated at 100° C. for 3 minutes, and then avowed to stand for 1 hour or more to return the temperature to room temperature. 160 μL of the sample was transferred to a dedicated cell, and the absorbance at 260 nm in association with dissociation to a single strand was measured while changing the temperature from 5° C. to 80° C. (0.5° C./min), and a 50% melting temperature (Tm) was calculated as described above. The results are shown in Table 3. Table 3 also shows a difference (ΔTm) in Tm of each siRNA with respect to Tm of siRNA 1, which is an evaluation criterion. The drawing results of the melting curves are also shown in FIG. 1.

TABLE 3

| No. | Sense Strand (5'→3')<br>Antisense Strand (3'→5') | Tm<br>(° C.) | ΔTm<br>(° C.) |
|---|---|---|---|
| siRNA 1 | GGCCUUUCACUCAUACUU<br>TTCCGGAAAGUGAUGAGGAUG | 79.0 | — |
| siRNA 2 | GGCCUUUCACUACUAAU$^{Ap}$ACUU<br>TTCCGGAAAGUGAUGAGGAUG | 77.2 | −1.8 |
| siRNA 3 | GGCCUUUCACU$^{Ap}$ACUAAUACUU<br>TTCCGGAAAGUGAUGAGGAUG | 77.3 | −1.7 |
| SIRNA 4 | GGCCUUU$^{Ap}$CACUACUAAUACUU<br>TTCCGGAAAGUGAUGAGGAUG | 77.2 | −1.8 |
| siRNA 5 | GGCCUUUCACUACUAAU$^{Aetx}$ACUU<br>TTCCGGAAAGUUAUGAGGAUG | 78.5 | −0.5 |
| siRNA 6 | GGCCUUUCACU$^{Aetx}$ACUAAUACUU<br>TTCCGGAAAGUGAUGAGGAUG | 78.5 | −0.5 |
| siRNA 7 | GGCCUUU$^{Aetx}$CACUACUAAUACUU<br>TTCCGGAAAGUGAUGAGGAUG | 78.5 | −0.5 |

As shown in Table 3, when compared with siRNA 1 (positive control), siRNAs 2 to 4 each having $U^{Ap}$ introduced decreased the Tm by 1.7 to 1.8° C., whereas siRNAs 5 to 7 each having $U^{Aetx}$ introduced decreased the Tm by only 0.5° C., which confirmed that they have the thermal stability equivalent to that of siRNA 1.

Evaluation of Sugar Moiety Puckering

To verify whether sugar moiety puckering affects the improvement of the thermal stability of the double-strand, a monomer of each of 2'-OMe-4'-aminoethoxyuridine, 2'-OMe-4'-aminopropoxyuridine and 2'-OMe-4'-aminopropyluridine was synthesized, and $^1$H NMR of the monomer was measured, and a value of $J_{1'-2'}$ was introduced into the following equation [1] to calculate the sugar moiety puckering (a ratio of N type present):

$$C3'\text{-endo (a ratio of N type present) [\%]} = 100 - (J_{1'\text{-}2'} \times 10) \quad [1]$$

Table 4 shows the above evaluation results.

TABLE 4

| Monomers | Ratio of N Type (%) |
|---|---|
| 2'-OMe-4'-aminoethoxyuridine | 68 |
| 2'-OMe-4'-aminopropyluridine | 22 |

As shown in Table 4, 2'-OMe-4'-aminoethoxyuridine had a higher ratio of N-type present than that of 2'-OMe-4'-aminopropyluridine. Therefore, the thermal stability of the double strand would be improved by increasing the ratio of the N type present.

Each of the monomers synthesized in the above evaluation was synthesized as follows:

Synthesis of Monomer (1) Monomer of 2'-OMe-4'-aminoethoxyuridine

A monomer was synthesized in which the group —O—$C_2H_4$—NH-TFA at the 4' position of 5-O-[bis(4-methoxyphenyl)phenylmethyl]-4'-C-trifluoroacetylaminoethoxyl-2'-O-methyl-uridine (compound 11) was changed to a group —O—$C_2H_4$—$NH_2$. More particularly, the monomer was synthesized by the following scheme. To a solution of compound 11 (0.15 g, 0.28 mmol) in tetrahydrofuran (1.35 mL) was added a tetrahydrofuran solution of 1 M tetrabutylammonium fluoride (TBAF, 0.43 mL, 0.43 mmol) in an Ar atmosphere, and stirred at room temperature for 4 hours. Subsequently, ammonia water (1 mL, 26 mmol) was added to the reaction mixture, and incubated at 55° C. for 4 hours to obtain a monomer.

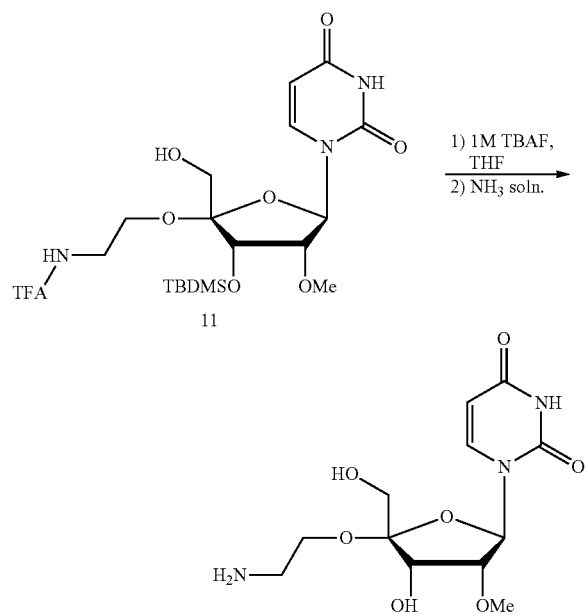

(2) Monomer of 2'-OMe-4'-aminopropyluridine

A monomer was synthesized in which the group —$C_3H_6$—NH-TFA at the 4' position of 5-O-[bis(4-methoxyphenyl)phenylmethyl]-4'-C-trifluoroacetylaminopropyl-2'-O-methyl-uridine (compound 26) was changed to a group —$C_3H_6$—$NH_2$. More particularly, the monomer was synthesized by the following scheme:

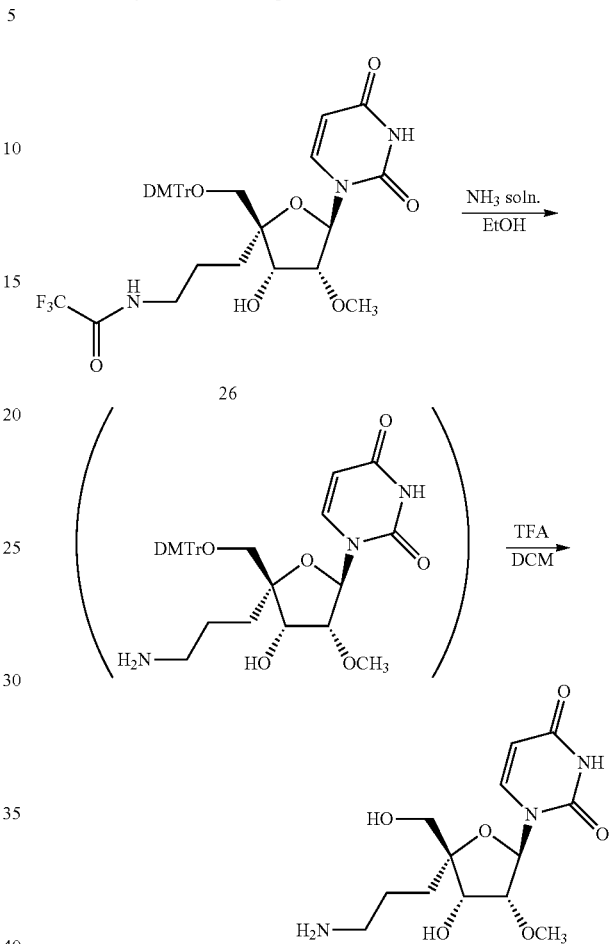

Evaluation of RNA Interference Ability

RNA interference ability was evaluated using siRNAs 1 to 7 synthesized above. A Dual luciferase reporter assay was used to evaluate the RNA interference ability of each siRNA. HeLa cells (strain stably expressing Firefly luciferase and Renilla luciferase) were prepared to provide $8.0 \times 10^3$ cells/mL, and 100 μL of the cells was placed in each of 96 well plates and cultured for 24 hours. Each strand of the synthesized siRNAs was dissolved in TE buffer (10 μL), heated at 95° C. for 3 minutes, and then allowed to stand for 1 hour or more to return the temperature to room temperature. Each amount of siRNAs thus obtained, each amount of media (OPTI-MEM), and 1.5 μL of lipofectamine RNAiMAX (transfection reagent) were mixed so as to have a total amount of 50 μL, and 10 μL of the mixture was placed in each of the well plates that had sucked the media, and cultured in a $CO_2$ incubator at 37° C. for 20 minutes, and 50 μL of medium was then added and cultured in a $CO_2$ incubator at 37° C. for 24 hours. After 24 hours, the medium was sucked and cryopreserved. Each siRNA was evaluated at two concentrations of 1 nM and 10 nM.

For the measurement of luciferase luminescence, after thawing, 24 μL of Dual glo substrate (a substrate for Firefly luciferase) was added and allowed to stand for 5 minutes, and 23 μL of the sample was then transferred to 96 well plates for measuring luminescence, and the Firefly luciferase was measured. Subsequently, 23 μL of Stop and glo substrate (a substrate for Renilla luciferase) was added, and allowed to stand for 10 minutes, and Renilla luciferase was then measured. The measured luminescence values of Renilla luciferase were divided by the values of Firefly luciferase and compared using the % of control. In addition, luciferase JNR II was used for the luciferase measurement. The results are shown in FIG. 3.

Figure 3:
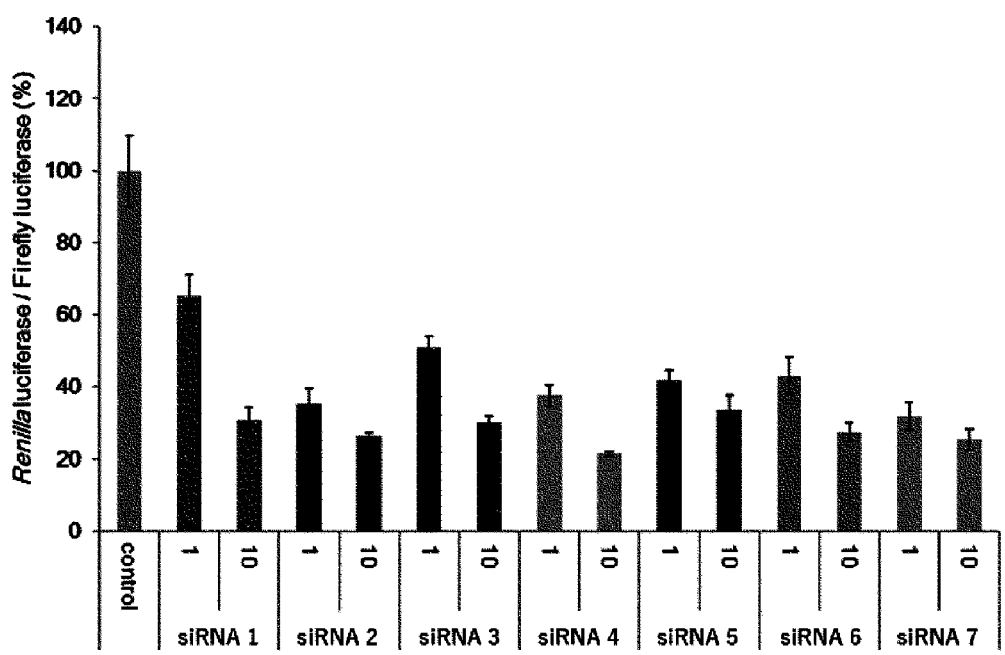
FIG. 3 is evaluation results of RNA interference ability of siRNAs 1 to 7 synthesized in Examples.

As shown in FIG. 3, siRNAs 5 to 7 each having $U^{Aetx}$ introduced showed the same level of gene expression inhibitory ability as that of siRNA 1 (positive control), as with siRNAs 2 to 4 each having $U^{Ap}$ introduced.

As can be seen from the above results, when used as a component such as double-stranded RNA, the nucleoside derivative or salt thereof according to the present invention can provide an oligonucleotide derivative or a salt thereof having higher thermal stability. Further, the oligonucleotide derivative or salt thereof according to the present invention can have higher thermal stability when forming double-stranded RNA, and have sufficient gene expression inhibitory ability as a nucleic acid drug such as siRNA.

Sequence Listing Free Text

SEQ ID NO: 1: Sense strand RNA of Duplexes 1-3 synthesized in Examples;
SEQ ID NO: 2: Antisense strand RNA of Duplexes 1-3 synthesized in Examples;
SEQ ID NO: 3: Sense strand DNA of Duplexes 4-5 synthesized in Examples;
SEQ ID NO: 4: Antisense strand RNA of Duplexes 4-5 synthesized in Examples;
SEQ ID NO: 5: Sense strand RNA of siRNAs 1-7 synthesized in Examples; and
SEQ ID NO: 6: Antisense strand DNA of siRNAs 1-7 synthesized in Examples.

The invention claimed is:

1. A nucleoside derivative represented by the following formula (1):

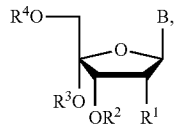

or a salt thereof, wherein $R^1$ represents a methoxy group; $R^2$ and $R^4$, which may be the same as or different from each other, each represents a hydrogen atom, a protective group for a hydroxyl group, a phosphate group, a protected phosphate group, or —P(=O)$_n$R$^5$R$^6$ in which n represents 0 or 1, $R^5$ and $R^6$, which may be the same as or different from each other, each represents a hydrogen atom, a hydroxyl group, a protected hydroxyl group, a mercapto group, a protected mercapto group, an alkoxy group, a cyanoalkoxy group, an amino group, or a substituted amino group, provided that when n is 1, both $R^5$ and $R^6$ cannot be the hydrogen atom at the same time; $R^3$ represents —(CH$_2$)$_m$NHR$^7$ in which m represents 2, $R^7$ represents a hydrogen atom, an alkyl group, an alkenyl group or a protective group for an amino group; and B represents a purin-9-yl group, a 2-oxo-pyrimidin-1-yl group, a substituted purin-9-yl group, or a substituted 2-oxo-pyrimidin-1-yl group.

2. The nucleoside derivative or the salt thereof according to claim 1, wherein $R^7$ represents a hydrogen atom.

3. An oligonucleotide derivative comprising at least one partial structure represented by the following formula (2):

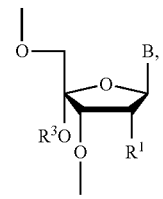

or a salt thereof, wherein, $R^1$ represents a methoxy group; $R^3$ represents —(CH$_2$)$_m$NHR$^7$ in which m represents 2, and $R^7$ represents a hydrogen atom, an alkyl group, an alkenyl group, or a protective group for an amino group; and B represents a purin-9-yl group, a 2-oxo-pyrimidin-1-yl group, a substituted purin-9-yl group, or a substituted 2-oxo-pyrimidin-1-yl group.

4. The oligonucleoside derivative or the salt thereof according to claim 3, wherein $R^7$ represents a hydrogen atom.

5. An siRNA comprising the oligonucleotide derivative or the salt thereof according to claim 3 as an active ingredient.

* * * * *